United States Patent
Larsen et al.

(10) Patent No.: US 12,037,548 B2
(45) Date of Patent: *Jul. 16, 2024

(54) METHODS AND SYSTEMS FOR ENHANCING PROCESSING OF HYDROCARBONS IN A FLUID CATALYTIC CRACKING UNIT USING A RENEWABLE ADDITIVE

(71) Applicant: MARATHON PETROLEUM COMPANY LP, Findlay, OH (US)

(72) Inventors: Nikolas A. Larsen, Findlay, OH (US); Jeffrey A. Sexton, Findlay, OH (US)

(73) Assignee: MARATHON PETROLEUM COMPANY LP, Findlay, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/210,778

(22) Filed: Jun. 16, 2023

(65) Prior Publication Data
US 2023/0332056 A1 Oct. 19, 2023

Related U.S. Application Data

(63) Continuation-in-part of application No. 18/045,314, filed on Oct. 10, 2022, now Pat. No. 11,692,141.
(Continued)

(51) Int. Cl.
*C10G 11/18* (2006.01)
*C07C 4/06* (2006.01)

(52) U.S. Cl.
CPC .............. *C10G 11/187* (2013.01); *C07C 4/06* (2013.01); *C10G 11/182* (2013.01);
(Continued)

(58) Field of Classification Search
CPC .............. C07C 4/06; C10G 2300/4093; C10G 2300/708; C10G 2400/02; C10G 2400/20
See application file for complete search history.

(56) References Cited

U.S. PATENT DOCUMENTS 2,792,908 A 5/1957 Glanzer
2,804,165 A 8/1957 Blomgren
(Continued)

FOREIGN PATENT DOCUMENTS

AT 11772 U1 4/2011
CN 201264907 Y 7/2009
(Continued)

OTHER PUBLICATIONS

Bollas, G.M., et al., 2002, Industrial and Engineering Chemistry Research, 41(22), 5410-5419. https://doi.org/10.1021/ie0202423 (Year: 2002).*
(Continued)

*Primary Examiner* — Brian A McCaig
(74) *Attorney, Agent, or Firm* — Womble Bond Dickinson (US) LLP

(57) ABSTRACT

Methods and systems for enhancing hydrocarbon processing in a fluid catalytic cracking (FCC) unit by introducing a renewable feedstock into the FCC unit at alternative locations of the FCC unit to increase residence time and promote a higher degree of FCC feedstock cracking. The renewable feedstock may include one or more of plastic-derived pyrolysis oil or plastic-derived hydrocarbons, biomass-derived pyrolysis oil, municipal waste-derived pyrolysis oil, vegetable based feedstock, animal fat feedstock, algae oil, sugar-derived hydrocarbons, or carbohydrate-derived hydrocarbons. The alternative locations of the FCC unit may include one or more of FCC reactor catalyst bed, an FCC catalyst stripper, at a nozzle located downstream of a gas oil injection point, or at a nozzle located upstream of the gas oil injection point.

30 Claims, 5 Drawing Sheets

Related U.S. Application Data

(60) Provisional application No. 63/495,761, filed on Apr. 12, 2023, provisional application No. 63/495,748, filed on Apr. 12, 2023, provisional application No. 63/378,981, filed on Oct. 10, 2022, provisional application No. 63/262,342, filed on Oct. 10, 2021.

(52) U.S. Cl.
CPC ........... *C10G 2300/4093* (2013.01); *C10G 2300/708* (2013.01); *C10G 2400/02* (2013.01); *C10G 2400/20* (2013.01)

(56) References Cited

U.S. PATENT DOCUMENTS

| | | |
|---|---|---|
| 2,867,913 A | 1/1959 | Faucher |
| 2,925,144 A | 2/1960 | Kroll |
| 3,901,951 A | 8/1975 | Nishizaki |
| 4,066,425 A | 1/1978 | Nett |
| 4,217,116 A | 8/1980 | Seever |
| 5,115,686 A | 5/1992 | Walker et al. |
| 5,302,294 A | 4/1994 | Schubert |
| 5,415,025 A | 5/1995 | Bartman et al. |
| 5,443,716 A | 8/1995 | Anderson et al. |
| 5,446,681 A | 8/1995 | Gethner et al. |
| 5,516,969 A | 5/1996 | Krasznai et al. |
| 5,540,893 A | 7/1996 | English |
| 6,258,987 B1 | 7/2001 | Schmidt et al. |
| 7,194,369 B2 | 3/2007 | Lundstedt et al. |
| 7,682,501 B2 | 3/2010 | Soni et al. |
| 7,931,803 B2 | 4/2011 | Buchanan |
| 7,932,424 B2 | 4/2011 | Fujimoto et al. |
| 7,981,361 B2 | 7/2011 | Bacik |
| 8,518,131 B2 | 8/2013 | Mattingly et al. |
| 8,569,068 B2 | 10/2013 | Carpenter et al. |
| 8,753,502 B1 | 6/2014 | Sexton et al. |
| 8,829,258 B2 | 9/2014 | Gong et al. |
| 8,999,012 B2 | 4/2015 | Kelly et al. |
| 9,109,177 B2 | 8/2015 | Freel et al. |
| 9,279,748 B1 | 3/2016 | Hughes et al. |
| 9,428,695 B2 | 8/2016 | Narayanaswamy et al. |
| 9,662,597 B1 | 5/2017 | Formoso |
| 9,663,729 B2 | 5/2017 | Baird et al. |
| 9,789,290 B2 | 10/2017 | Forsell |
| 9,925,486 B1 | 3/2018 | Botti |
| 10,384,157 B2 | 8/2019 | Balcik |
| 10,435,339 B2 | 10/2019 | Larsen et al. |
| 10,479,943 B1 | 11/2019 | Liu et al. |
| 10,563,130 B2 | 2/2020 | Narayanaswamy et al. |
| 10,570,078 B2 | 2/2020 | Arsen et al. |
| 10,640,719 B2 | 5/2020 | Freel et al. |
| 11,164,406 B2 | 11/2021 | Meroux et al. |
| 11,214,741 B2 | 1/2022 | Davydov et al. |
| 11,306,253 B2 | 4/2022 | Timken et al. |
| 11,319,262 B2 | 5/2022 | Wu et al. |
| 11,421,162 B2 | 8/2022 | Pradeep et al. |
| 11,578,638 B2 | 2/2023 | Thobe |
| 11,692,141 B2 | 7/2023 | Larsen et al. |
| 11,702,600 B2 | 7/2023 | Sexton et al. |
| 11,715,950 B2 | 8/2023 | Miller et al. |
| 11,720,526 B2 | 8/2023 | Miller et al. |
| 11,802,257 B2 | 10/2023 | Short et al. |
| 11,835,450 B2 | 12/2023 | Bledsoe, Jr. et al. |
| 11,860,069 B2 | 1/2024 | Bledsoe, Jr. |
| 11,891,581 B2 | 2/2024 | Cantley et al. |
| 11,898,109 B2 | 2/2024 | Sexton et al. |
| 11,905,468 B2 | 2/2024 | Sexton et al. |
| 11,905,479 B2 | 2/2024 | Eller et al. |
| 11,906,423 B2 | 2/2024 | Bledsoe, Jr. |
| 11,920,096 B2 | 3/2024 | Woodchick et al. |
| 11,921,035 B2 | 3/2024 | Bledsoe, Jr. et al. |
| 11,970,664 B2 | 4/2024 | Larsen |
| 2004/0139858 A1 | 7/2004 | Entezarian |
| 2005/0143609 A1 | 6/2005 | Wolf et al. |
| 2005/0229777 A1 | 10/2005 | Brown |
| 2006/0091059 A1 | 5/2006 | Barbaro |
| 2007/0112258 A1 | 5/2007 | Soyemi et al. |
| 2008/0087592 A1 | 4/2008 | Buchanan |
| 2010/0166602 A1 | 7/2010 | Bacik |
| 2010/0318118 A1 | 12/2010 | Forsell |
| 2012/0222550 A1 | 9/2012 | Ellis |
| 2012/0272715 A1 | 11/2012 | Kriel et al. |
| 2013/0112313 A1 | 5/2013 | Donnelly et al. |
| 2013/0192339 A1 | 8/2013 | Kriel et al. |
| 2014/0041150 A1 | 2/2014 | Sjoberg |
| 2014/0121428 A1 | 5/2014 | Wang et al. |
| 2014/0316176 A1 | 10/2014 | Fjare et al. |
| 2015/0005547 A1 | 1/2015 | Freel et al. |
| 2015/0005548 A1 | 1/2015 | Freel et al. |
| 2015/0034570 A1 | 2/2015 | Andreussi |
| 2015/0166426 A1 | 6/2015 | Wegerer et al. |
| 2015/0240167 A1 | 8/2015 | Kulprathipanja et al. |
| 2015/0337207 A1 | 11/2015 | Chen et al. |
| 2016/0045918 A1 | 2/2016 | Lapham |
| 2016/0090539 A1 | 3/2016 | Frey et al. |
| 2016/0168481 A1 | 6/2016 | Ray et al. |
| 2016/0175749 A1 | 6/2016 | Suda |
| 2016/0244677 A1 | 8/2016 | Froehle |
| 2016/0312127 A1 | 10/2016 | Frey et al. |
| 2017/0151526 A1 | 6/2017 | Cole |
| 2017/0269559 A1 | 9/2017 | Trygstad |
| 2018/0371325 A1 | 12/2018 | Streiff et al. |
| 2020/0041481 A1 | 2/2020 | Burgess |
| 2020/0181502 A1 | 6/2020 | Paasikallio et al. |
| 2020/0246743 A1 | 8/2020 | Sorensen |
| 2020/0316513 A1 | 10/2020 | Zhao |
| 2021/0103304 A1 | 4/2021 | Fogarty et al. |
| 2021/0213382 A1 | 7/2021 | Cole |
| 2021/0301210 A1 | 9/2021 | Timken et al. |
| 2022/0041940 A1 | 2/2022 | Pradeep et al. |
| 2022/0299170 A1 | 9/2022 | Raynor et al. |
| 2022/0343229 A1 | 10/2022 | Gruber et al. |
| 2022/0357303 A1 | 11/2022 | Zhu et al. |
| 2023/0015077 A1 | 1/2023 | Kim |
| 2023/0078852 A1 | 3/2023 | Campbell et al. |
| 2023/0220286 A1 | 7/2023 | Cantley et al. |
| 2023/0241548 A1 | 8/2023 | Holland et al. |
| 2023/0242837 A1 | 8/2023 | Short et al. |
| 2023/0259080 A1 | 8/2023 | Whikehart et al. |
| 2023/0259088 A1 | 8/2023 | Borup et al. |
| 2023/0272290 A1 | 8/2023 | Larsen et al. |
| 2023/0295528 A1 | 9/2023 | Eller et al. |
| 2023/0332058 A1 | 10/2023 | Larsen et al. |
| 2023/0357649 A1 | 11/2023 | Sexton et al. |
| 2023/0400184 A1 | 12/2023 | Craig |
| 2023/0416615 A1 | 12/2023 | Larsen |
| 2023/0416638 A1 | 12/2023 | Short |
| 2024/0011898 A1 | 1/2024 | Bledsoe, Jr. et al. |
| 2024/0115996 A1 | 4/2024 | Rudd |
| 2024/0117262 A1 | 4/2024 | Eller |
| 2024/0118194 A1 | 4/2024 | Bledsoe, Jr |
| 2024/0124790 A1 | 4/2024 | Sexton |
| 2024/0132786 A1 | 4/2024 | Sexton |

FOREIGN PATENT DOCUMENTS

| | | | |
|---|---|---|---|
| CN | 111336612 A | 6/2020 | |
| CN | 213824075 U | 7/2021 | |
| CN | 215263512 U | 12/2021 | |
| CN | 215288592 | 12/2021 | |
| DE | 102014009231 A1 | 1/2016 | |
| EP | 1870153 | 12/2007 | |
| EP | 3878926 | 9/2021 | |
| FR | 2357630 | 2/1978 | |
| WO | 94/08225 | 4/1994 | |
| WO | 2002038295 | 5/2002 | |
| WO | 2010/144191 | 12/2010 | |
| WO | 2012062924 | 5/2012 | |
| WO | 2017207976 | 12/2017 | |
| WO | WO-2018017664 A1 * | 1/2018 | ............ C10G 11/00 |
| WO | WO-2020035797 A1 * | 2/2020 | ............ C10G 11/18 |
| WO | 2022149501 | 7/2022 | |
| WO | 20220144495 | 7/2022 | |
| WO | 2022219234 | 10/2022 | |

(56) References Cited

FOREIGN PATENT DOCUMENTS

| WO | 2022220991 | 10/2022 |
|---|---|---|
| WO | 2023038579 | 3/2023 |
| WO | 2023137304 | 7/2023 |
| WO | 2023164683 | 8/2023 |
| WO | 2023242308 | 12/2023 |

OTHER PUBLICATIONS

Voutetakis, S.S., et al., 1996, Computers & Chemical Engineering, 20 Suppl., S1301-S1606. https://doi.org/10.1016/0098-1354(96)00272-4 (Year: 1996).*

Andrea De Rezende Pinho et al., Fast pyrolysis oil from pinewood chips co-processing with vacuum gas oil in an FCC unit for second generation fuel production, Fuel 188 (2017) 462-473.

Passamonti, Francisco J et al., Recycling of waste plastics into fuels. LDPE conversion in FCC, Applied Catalysis B: Environmental 125 (2012) 499-506.

Rodriguez, Elena et al., Coke deposition and product distribution in the co-cracking of waste polyolefin derived streams and vacuum gas oil under FCC unit conditions, Fuel Processing Technology 192 (2019) 130-139.

Lloyd's Register, Using technology to trace the carbon intensity of sustainable marine fuels, Feb. 15, 2023.

"Development of Model Equations for Predicting Gasoline Blending Properties", Odula et al., American Journal of Chemical Engineering, vol. 3, No. 2-1, 2015, pp. 9-17.

Pashikanti et al., "Predictive modeling of large-scale integrated refinery reaction and fractionation systems from plant data. Part 3: Continuous Catalyst Regeneration (CCR) Reforming Process," Energy & Fuels 2011, 23, 5320-5344 (Year: 2011).

Swagelok, Grab Sampling Systems Application Guide, 53 pages.

Frank et al., "Fuel Tank and Charcoal Canister Fire Hazards during EVAP System Leak Testing", SAE International, 2007 World Congress, Detroit, Michigan, Apr. 16-19, 2007, 11 pages.

Doolin et al., "Catalyst Regeneration and Continuous Reforming Issues", Catalytic Naptha Reforming, 2004.

* cited by examiner

METHODS AND SYSTEMS FOR ENHANCING PROCESSING OF HYDROCARBONS IN A FLUID CATALYTIC CRACKING UNIT USING A RENEWABLE ADDITIVE

CROSS-REFERENCE TO RELATED APPLICATIONS

The present application claims priority to and the benefit of U.S. Provisional Application No. 63/378,981, filed Oct. 10, 2022, titled "METHODS AND SYSTEMS FOR ENHANCING PROCESSING OF HYDROCARBONS IN A FLUID CATALYTIC CRACKING UNIT USING A RENEWABLE ADDITIVE," U.S. Provisional Application No. 63/495,761, filed Apr. 12, 2023, titled "METHODS AND SYSTEMS FOR ENHANCING PROCESSING OF HYDROCARBONS IN A FLUID CATALYTIC CRACKING UNIT USING PLASTIC," and U.S. Provisional Application No. 63/495,748, filed Apr. 12, 2023, titled "METHODS AND SYSTEMS FOR ENHANCING PROCESSING OF HYDROCARBONS IN A FLUID CATALYTIC CRACKING UNIT USING A RENEWABLE ADDITIVE," the disclosures of which are incorporated herein by reference in their entirety. This application is also a continuation-in-part of U.S. Non-Provisional application Ser. No. 18/045,314, filed Oct. 10, 2022, titled "METHODS AND SYSTEMS FOR ENHANCING PROCESSING OF HYDROCARBONS IN A FLUID CATALYTIC CRACKING UNIT USING A RENEWABLE ADDITIVE," which claims priority to and the benefit of U.S. Provisional Application No. 63/262,342, filed Oct. 10, 2021, titled "METHODS AND SYSTEMS FOR ENHANCING PROCESSING OF HYDROCARBONS IN A FLUID CATALYTIC CRACKING UNIT USING A RENEWABLE ADDITIVE," the disclosures of which are incorporated herein by reference in their entirety.

TECHNICAL FIELD

This disclosure relates to systems and methods for enhancing the processing of hydrocarbons in a fluid catalytic cracking (FCC) unit by introduction of a renewable feedstock to the FCC unit to improve production of propylene and/or plastic precursors. The disclosure relates to the addition of certain specific renewable feedstock as an additive to the FCC unit.

BACKGROUND

FCC units are used in refining operations to produce gasoline and distillate fuels from higher molecular weight hydrocarbons. A catalytic FCC unit has two main components—a reactor and a regenerator. Severe hydroprocessing of FCC feedstock, which is utilized to meet gasoline sulfur specifications, can result in low FCC regenerator temperatures, low delta coke, and become an obstacle or constraint to unit optimization and refinery profitability.

Further, co-processing of certain pyrolysis oils in the FCC riser of the FCC reactor is thought to cause several issues or have several challenges. For example, bio-mass derived pyrolysis oil and/or other renewable feedstock may cause stability/miscibility issues when the biomass-derived pyrolysis oil and/or other renewable feedstock are mixed with the FCC feed and may include a potential to coke/plug when mixed at elevated temperatures. Certain studies have shown the development of 'tar balls' in the FCC stripper of the FCC reactor and more deposits in the FCC reactor were noted upon cleaning/inspection. Further still, some pyrolysis oils may cause potential corrosion of stainless steel in the FCC riser of the FCC reactor. In addition to the corrosion concerns, co-processing of pyrolysis oil in a FCC riser may result in significant amounts of oxygenates in the FCC hydrocarbon products. Increases in CO and $CO_2$ may also exacerbate a FCC unit wet gas compressor constraint (commonly encountered in FCC units) and reduce unit/refinery profitability. Generation of water pulls hydrogen from going to liquid hydrocarbon products, thus leading to reduced FCC unit and refinery profitability. Oxygenates remaining in hydrocarbon products may also increase corrosion and/or operability concerns.

SUMMARY

Provided here are systems and methods to address these shortcomings of the art and provide other additional or alternative advantages. The disclosure herein provides one or more embodiments of systems and methods for enhancing the processing of hydrocarbons in a FCC unit by introduction of a renewable feed or feedstock to alternative locations of the FCC unit to improve production of propylene and/or plastic precursors. In embodiments, the renewable feedstock provided as an additive to the FCC unit may comprise one or more of plastic-derived pyrolysis oil, plastic-based oil or plastic-based hydrocarbons refined via other methods (for example, the other methods including, but not limited to, hydrothermal processing, liquefaction, gasification, catalytic degradation, and/or other methods suitable for generating oil or another fluid from plastic, as will be understood by one skilled in the art), biomass-derived pyrolysis oil, municipal waste-derived pyrolysis oil, vegetable based feedstock, animal fat feedstock, algae oil, sugar-derived hydrocarbons, or carbohydrate-derived hydrocarbons. The alternative locations of the FCC unit may comprise one or more of FCC reactor catalyst bed, an FCC catalyst stripper, a regenerator of the FCC, at a nozzle located above or downstream of a gas oil injection point, at a nozzle located below or upstream of the gas oil injection point, and/or at various points where steam is introduced into the FCC unit (for example, stripping steam, pre-stripping steam, or fluffing steam). Injection of the renewable feedstock may be via a dedicated nozzle positioned at each of the alternative locations and/or, as noted, with steam. Pyrolysis oil can be utilized as a FCC feedstock additive and is a low sulfur content material that, despite its traditional characteristics of low miscibility with hydrocarbons and high acidity, may be used to generate selective yields for production of various hydrocarbon based products (such as, for example, propylene and/or plastic precursors). Design modifications are provided for new and/or existing FCC units or reactors to enhance selective yields of the FCC unit, increase residence time, promote a higher than typical degree of cracking, and/or reduce coke formation. Such systems and methods may advantageously provide for consumption of renewable feedstocks in a FCC unit, decrease the energy consumption of a FCC regenerator, and increase FCC unit and refinery profitability.

In certain embodiments, hydrocarbon processing in a FCC unit may be enhanced by first introducing gas oil and steam into the riser of a FCC unit. The gas oil and steam may be mixed with a catalyst that is fluidized in the riser. Prior to and/or after the mixing, a renewable feedstock may be injected into the FCC unit at one or more alternative locations of the FCC unit. The gas oil and renewable feedstock may be cracked into one or more FCC products in the presence of the catalyst and the steam, which may cause one or more surfaces of the catalyst to be at least partially covered by coke. The coked FCC catalyst may be separated from the FCC products in a cyclone or cyclones of the FCC unit. The cyclone or cyclones may be positioned in an upper portion of the FCC unit. The coked FCC catalyst from the reactor (for example, via the cyclone or cyclones) of the FCC unit may be passed to a regenerator, where air (and, in some embodiments, a an additional amount of renewable feedstock) are introduced into the regenerator to combust the coke from the coked FCC catalyst. Through such combustion, the coke may be oxidized by oxygen in the air, thus leading to regeneration of the catalyst. This regenerated catalyst may be returned from the regenerator to the riser of the FCC unit. The FCC product may be passed to an outlet and further downstream for additional processing (for example, fractionation). The alternative locations may include or comprise one or more of injection points separate from the gas oil injection point, at a FCC reactor catalyst bed, at an FCC catalyst stripper, at a nozzle located above or downstream of a gas oil injection point, at a nozzle below or upstream of the gas oil injection point, and/or at various points where steam is introduced into the FCC unit (for example, the renewable feedstock may be injected along with stripping steam, pre-stripping steam, or fluffing steam). In embodiments, the renewable feedstock provided as an additive to the FCC regenerator may comprise one or more of plastic-derived pyrolysis oil, plastic-based oil or plastic-based hydrocarbons refined via other methods (for example, the other methods including, but not limited to, hydrothermal processing, liquefaction, gasification, catalytic degradation, and/or other methods suitable for generating oil or another fluid from plastic, as will be understood by one skilled in the art), biomass-derived pyrolysis oil, municipal waste-derived pyrolysis oil, vegetable based feedstock, animal fat feedstock, algae oil, sugar-derived hydrocarbons, or carbohydrate-derived hydrocarbons. Such renewable feedstocks may include low sulfur levels, thus enabling the use of the renewable feedstock in forming transportation fuel with specific sulfur specifications. Further, renewable feedstock may be more olefinic and have a lower initial and final boiling point than a typical feedstock. Further still, the renewable feedstock may include a blend of pyrolysis oil and wax.

Thus, an embodiment of the disclosure is directed to a method of processing a gas oil in a fluid catalytic cracking (FCC) unit. The method may include introducing the gas oil and steam into a riser of a FCC unit. The method may include mixing the gas oil and the steam with a FCC catalyst fluidized in the riser. The method may include injecting one or more renewable feedstock into the FCC unit and/or the riser of the FCC unit through one or more alternative locations of the FCC unit at one or more time periods. The method may include cracking the gas oil and one or more renewable feedstock into one or more FCC hydrocarbon products in the FCC unit, thereby to cause one or more surfaces of the FCC catalyst to be at least partially covered by coke so as to define a coked FCC catalyst. The method may include separating the coked FCC catalyst from the one or more FCC hydrocarbon products in a cyclone or cyclones of the FCC unit. The method may include passing the FCC hydrocarbon products from the cyclone or cyclones of the FCC unit to an outlet.

In an embodiment, the one or more alternative locations may comprise a nozzle or injection point separate from a gas oil injection point, at one or more of an FCC reactor catalyst bed, at an FCC catalyst stripper, at a regenerator, at a nozzle located above or downstream of a gas oil injection point, or at a nozzle below or upstream of the gas oil injection point. The injection of the one or more renewable feedstock occurs with or separate from one or more of a pre-stripping stream, a stripping steam, or a fluffing steam. The one or more alternative locations may, in another embodiment, comprise a location in the FCC unit where catalyst densities are greater than about 30 lbs/ft3. In an embodiment, injection of the one or more renewable feedstock at the location in the FCC unit where catalyst densities are greater than about 30 lbs/ft3 may cause an increase in residence time and promotes higher degrees of cracking the gas oil and the one or more renewable feedstock into lighter hydrocarbon products. The lighter hydrocarbon products may comprise one or more of naphtha or liquefied petroleum gas.

In an embodiment, the one or more renewable feedstock may comprise one or more of plastic-derived pyrolysis oil, plastic-derived oil or plastic-based hydrocarbons, biomass-derived pyrolysis oil, municipal waste-derived pyrolysis oil, vegetable based feedstock, animal fat feedstock, algae oil, sugar-derived hydrocarbons, or carbohydrate-derived hydrocarbons. Injection of the one or more renewable feedstock into the one or more alternative locations may generate selective yields for production of specified hydrocarbon products. The specified hydrocarbon products may include one or more of propylene, light olefins, transportation fuel, plastic precursors, or other petrochemical feedstock.

In an embodiment, the introduction of the one or more renewable feedstock may reduce or may increase delta coke based on a number of factors. For example, the type of renewable feedstock selected, as well as the quality of the renewable feedstock, may affect delta coke. Further, the alternative location may impact delta coke as well. Delta coke is a ratio of coke yield per a catalyst to oil (cat/oil) ratio. Delta coke may also be determined based on a weight or mass of regenerated catalyst transported from the regenerator to the reactor subtracted from the weight or mass of the coked catalyst being transferred from the reactor to the regenerator. Thus, as, for example, the cat/oil ratio increases, delta coke decreases.

For example, polyethylene or polypropylene based pyrolysis oil may be injected into the reactor of the FCC unit. In such examples, depending on the quality of the polyethylene or polypropylene based pyrolysis oil (in other words, the amount of contaminants in the polyethylene or polypropylene based pyrolysis oil) the delta coke may decrease or may not change in relation to delta coke levels prior to introduction of the polyethylene or polypropylene based pyrolysis oil, and, in some in embodiments, the delta coke may even increase (for example, injection of the polyethylene or polypropylene based pyrolysis oil into the stripper may increase delta coke).

In another example, a renewable feedstock may be added to the regenerator. Such an addition may increase the temperature within the regenerator. Further, due to the increased temperature more coke may be burned from the coked catalyst, as such, injection of renewable feedstock into the regenerator may increase the difference between the mass of coked catalyst entering the regenerator compared to the mass of regenerated catalyst leaving the regenerator, thus increasing the delta coke. In yet another example, the injection of the renewable feedstock into the regenerator may not change delta coke.

The one or more renewable feedstock may be injected in an amount ranging from about 1 to about 99 volume percent of the gas oil introduced into the riser of the FCC unit.

In another embodiment, the method may include determining, based on a signal received by a controller from a sensor and/or analyzer positioned at one or more of within the FCC unit, at the outlet of the FCC unit, or in fluid communication with the outlet of the FCC unit, one or more of a conversion, yield, or selectivity. The method may further include, in response to a determination that one or more of the conversion, yield, or selectivity are less than a preselected amount, adjusting an amount of the one or more renewable feedstock injected into the FCC unit at the one or more alternative locations.

Another embodiment of the disclosure is directed to a method of processing a gas oil in a fluid catalytic cracking (FCC) unit to increase yield selectivities (such as increasing yield of propylene, plastic precursors, and/or other feedstock). The method may include introducing the gas oil, a renewable feedstock, and steam into a riser of a FCC unit. The method may include mixing the gas oil, the renewable feedstock, and the steam with a catalyst fluidized in the riser. The method may include injecting an amount of another renewable feedstock into an alternative location of the FCC unit. The method may include cracking the gas oil, the renewable feedstock, and the another renewable feedstock into one or more hydrocarbon products in the FCC unit, thereby to cause one or more surfaces of the catalyst to be at least partially covered by coke so as to define a coked catalyst. The method may include separating the coked catalyst from the one or more hydrocarbon products, for example, in a cyclone or cyclones positioned in an upper portion of the FCC unit. The method may include passing the one or more hydrocarbon products to an outlet of the FCC unit.

In an embodiment, the method may further include passing the coked catalyst and an amount of unconverted renewable feedstock to a regenerator, for example, from a reactor or via the cyclone or cyclones of the FCC unit. The method may include introducing air into the regenerator. The method may include combusting the coke from the coked catalyst and the amount of unconverted renewable feedstock in the regenerator, thereby to oxidize via oxygen in the air and produce a regenerated catalyst and a flue gas. The method may include returning the regenerated catalyst from the regenerator to the riser of the FCC unit. The method may include injecting an additional amount of renewable feedstock into the regenerator.

In an embodiment, an amount of the renewable feedstock and an amount of the another renewable feedstock may be about 1% to about 99% of the gas oil. As one or more of the amount of renewable feedstock or the amount of the another renewable feedstock are increased, coke yields may decrease or increase based on where the renewable feedstock is injected. For example, if renewable feedstock is injected into the regenerator, the temperature within the regenerator may be increased. Such an increase may cause more coke to burn from the coked catalyst. Burning more coke from the coke catalyst may increase the difference between the mass of coked catalyst entering the regenerator compared to the mass of regenerated catalyst leaving the regenerator, thus increasing the delta coke, in one embodiment. The one or more of the amount of renewable feedstock or the amount of the another renewable feedstock include an olefinic content higher than that of the gas oil. The one or more of the amount of renewable feedstock or the amount of the another renewable feedstock may include a lower initial and final boiling point and a higher API gravity than that of the gas oil. One or more of the amount of renewable feedstock or the amount of the another renewable feedstock may include a blend of pyrolysis oil and wax. The blend may comprise about 60% to about 100% pyrolysis oil and about 40% to about 0% wax.

Another embodiment of the disclosure is directed to a method of processing a gas oil in a fluid catalytic cracking (FCC) unit. The method may include, during a FCC operation, injecting a selected amount of one or more renewable feedstock into one or more alternative locations of the FCC unit. The one or more alternative locations may comprise one or more of an FCC reactor catalyst bed, an FCC catalyst stripper, at a nozzle located downstream of a gas oil injection point, or at a nozzle located upstream of the gas oil injection point. The method may include cracking the gas oil and the one or more renewable feedstock into one or more FCC hydrocarbon products in the FCC unit, thereby to cause one or more surfaces of the FCC catalyst to be at least partially covered by coke so as to define a coked FCC catalyst. The method may include passing the FCC hydrocarbon products to an outlet for further use.

In another embodiment, the method may include passing the coked FCC catalyst to a regenerator of the FCC unit. The method may include introducing air and a second selected amount of one or more renewable feedstock into the regenerator. The method may include combusting the coke from the coked FCC catalyst and the amount of unconverted renewable feedstock in the regenerator, thereby to oxidize via oxygen in the air and produce a regenerated FCC catalyst and a flue gas. The method may include returning the regenerated FCC catalyst from the regenerator to a riser of the FCC unit.

In an embodiment, the one or more alternative locations may include one or more locations of the regenerator and such locations of the regenerator may enable introduction of the second selected amount of the one or more renewable feedstock into the regenerator to, in embodiments, control temperature of the FCC unit.

Another embodiment of the disclosure is directed to a system for processing a gas oil in a fluid catalytic cracking (FCC) unit. The system may include a riser having a first inlet to receive a gas oil stream, a second inlet to receive steam, a third inlet to receive a FCC catalyst, and a fourth inlet to receive a first renewable feedstock. The riser may be configured to be operated under cracking reaction pressure and temperature conditions to facilitate mixing and catalytic cracking of the gas oil stream in presence of the steam and the FCC catalyst to generate, produce, or yield a plurality of FCC products and coked FCC catalyst. The system may include a reactor having (i) a fifth inlet to receive a second renewable feedstock, (ii) a FCC reaction zone connected to and in fluid communication with the upper portion of the riser and operated to continue the cracking of the gas oil stream in presence of the steam and the FCC catalyst to form more of the plurality of FCC products and more of the coked FCC catalyst, (iii) a separation zone to separate the plurality of FCC products from the coked FCC catalyst, and (iv) a first outlet to transport the plurality of FCC products to a fractionation zone to separate the plurality of FCC products into one or more of propylene, isobutene, butylenes, gasoline, distillate, diesel fuel, heating oil, slurry oil, or wet gas.

The system may also include a regenerator connected to and in fluid communication with a second outlet of the reactor and having a sixth inlet to receive air, a third outlet being connected to and in fluid communication with the third inlet of the riser to supply a regenerated FCC catalyst to the riser, and a fourth outlet positioned to discharge a flue gas containing one or more of nitrogen, nitrogen oxides, carbon dioxide, carbon monoxide, or water vapor, the regenerator being operated to oxidize coke on the coked FCC catalyst, thereby to produce the regenerated FCC catalyst and the flue gas. The system may include a stripping zone connected to and in fluid communication with the second outlet and the regenerator, the stripping zone having a seventh inlet to receive a third renewable feedstock, the stripping zone being operated to remove adsorbed and entrained hydrocarbons from the coked FCC catalyst prior to supplying the coked FCC catalyst to the regenerator. The stripping zone may have an eighth inlet to receive stripping steam. A fourth renewable feedstock may be injected into the stripping zone with the stripping steam.

In another embodiment, a third renewable feedstock may be injected into the riser with regenerated FCC catalyst via the third outlet. In another embodiment, a third renewable feedstock may be injected into the riser with the steam. A third renewable feedstock is injected into one or more of the first inlet, the second inlet, or third inlet In an embodiment, the fourth inlet may be positioned above, downstream of, below, or upstream of the first inlet. In an embodiment, a fifth inlet may be in fluid communication with the FCC reaction zone or the separation zone.

Another embodiment of the disclosure is directed to a controller to control the processing a gas oil in a fluid catalytic cracking (FCC) unit. The controller may comprise a first set of one or more inputs in signal communication with one or more sensors positioned within one or more of a regenerator, a riser of an FCC unit, and/or a reactor of the FCC unit. The controller may receive signals from the one or more sensors indicative of a characteristic, the characteristic comprising one or more of temperature, pressure, composition, yield, and/or flow rate. The controller may comprise a first set of one or more inputs/outputs in signal communication with one or more flow control devices positioned on one or more inlets or outlets associated with the regenerator, the riser of the FCC unit, and/or the reactor of the FCC unit. The controller may, in response to the characteristic from one of the one or more sensors being less than or greater than a preselected threshold, adjust the one or more flow control devices via a signal indicating a new flow rate of renewable feedstock into one or more of the regenerator, the riser of the FCC unit, or the reactor of the FCC unit for the flow control device to adjust to.

In an embodiment, the controller may comprise a second input/output in signal communication with a flow control devices positioned on an outlet associated with the regenerator. The controller may be configured to, in response to the characteristic from one of the one or more sensors being less than or greater than a preselected threshold range, adjust, via a signal indicating a new flow rate for the flow control device to adjust to, flow of regenerated catalyst into the riser of the FCC unit via the flow control device.

These and other features, aspects, and advantages of the disclosure will be apparent from a reading of the following detailed description together with the accompanying drawings, which are briefly described below. The disclosure includes any combination of one or more features or elements set forth in this disclosure or recited in any one or more of the claims, regardless of whether such features or elements are expressly combined or otherwise recited in a specific embodiment description or claim herein. This disclosure is intended to be read holistically such that any separable features or elements of the disclosure, in any of its aspects and embodiments, should be viewed as intended to be combinable, unless the context of the disclosure clearly dictates otherwise.

BRIEF DESCRIPTION OF THE DRAWINGS

Figure 1A:
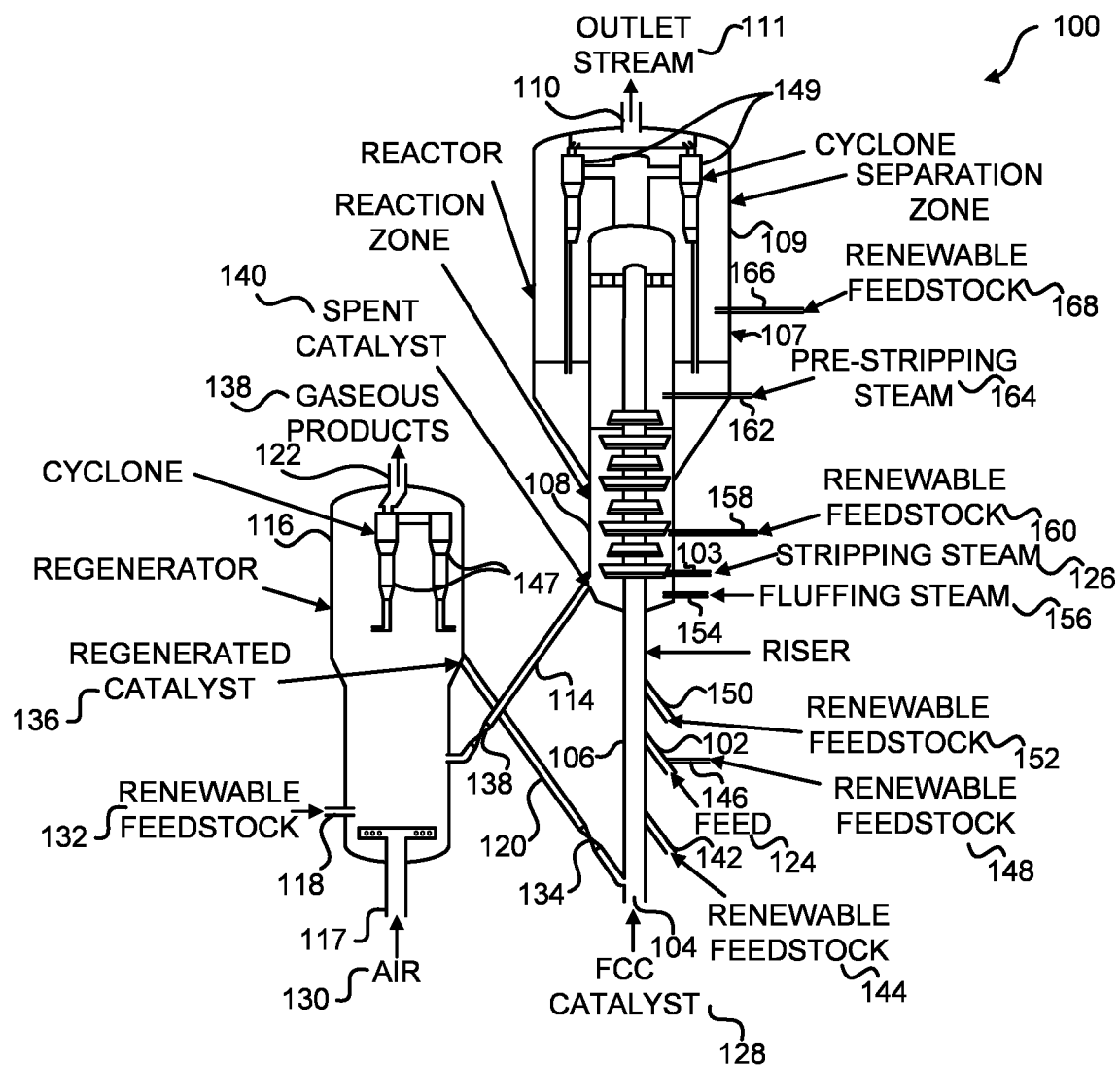
Figure 1B:
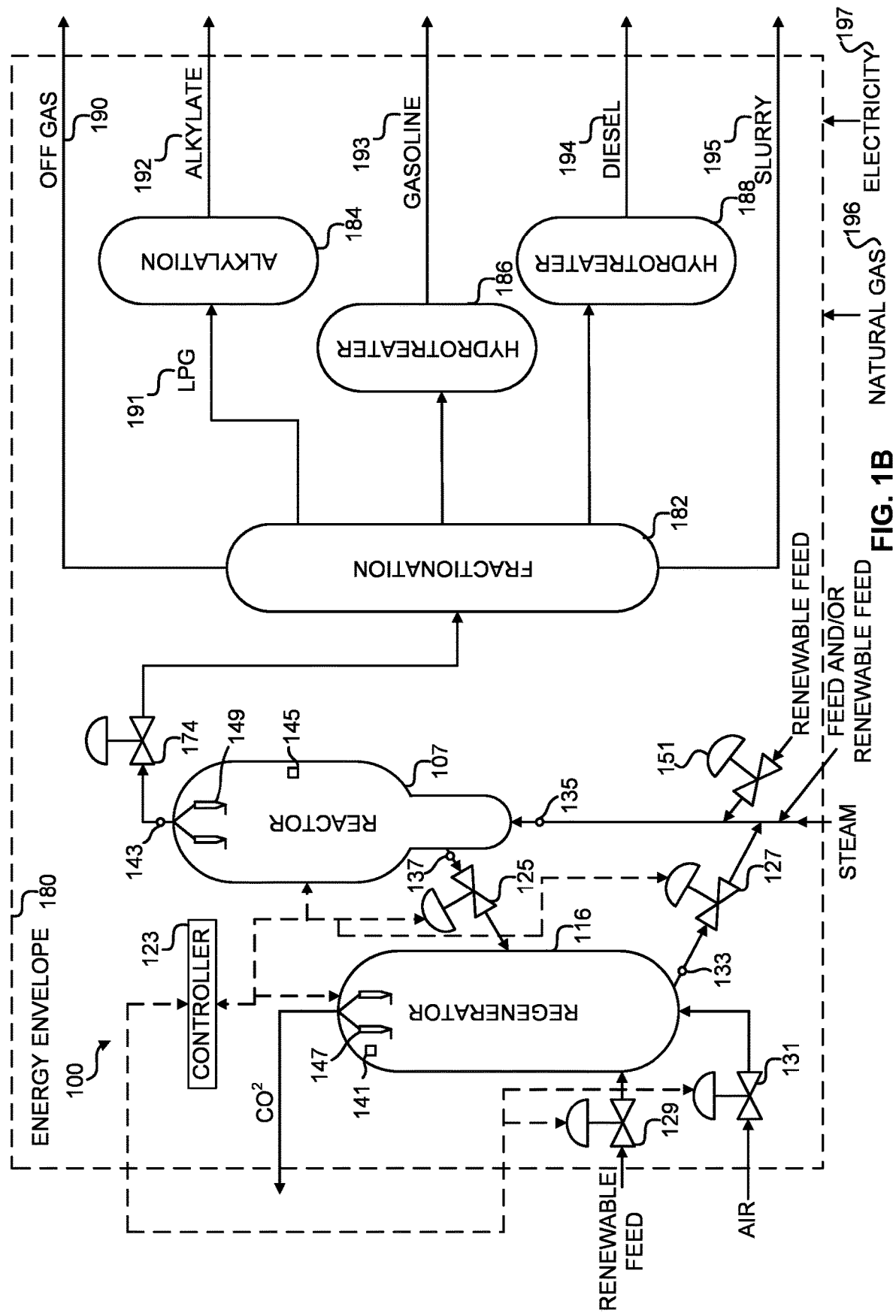

Having thus described the disclosure in general terms, reference will now be made to the accompanying drawings, which are not necessarily drawn to scale, and wherein:

FIG. 1A and FIG. 1B are schematic diagrams of a FCC unit, according to an embodiment of the disclosure.

Figure 2:
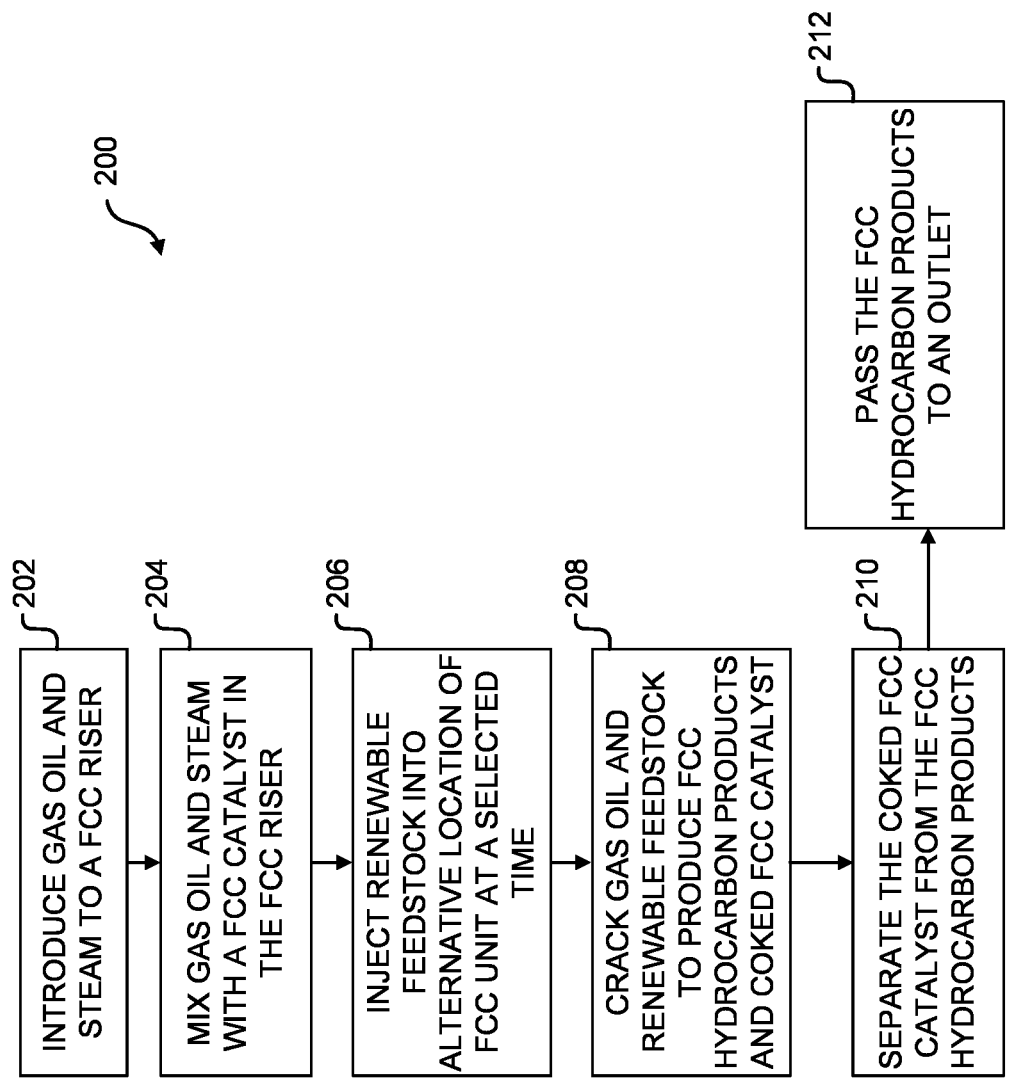

FIG. 2 is a block diagram of a method for processing of hydrocarbons in a FCC unit by introduction of a renewable feedstock into the FCC reactor, according to an embodiment of the disclosure.

Figure 3:
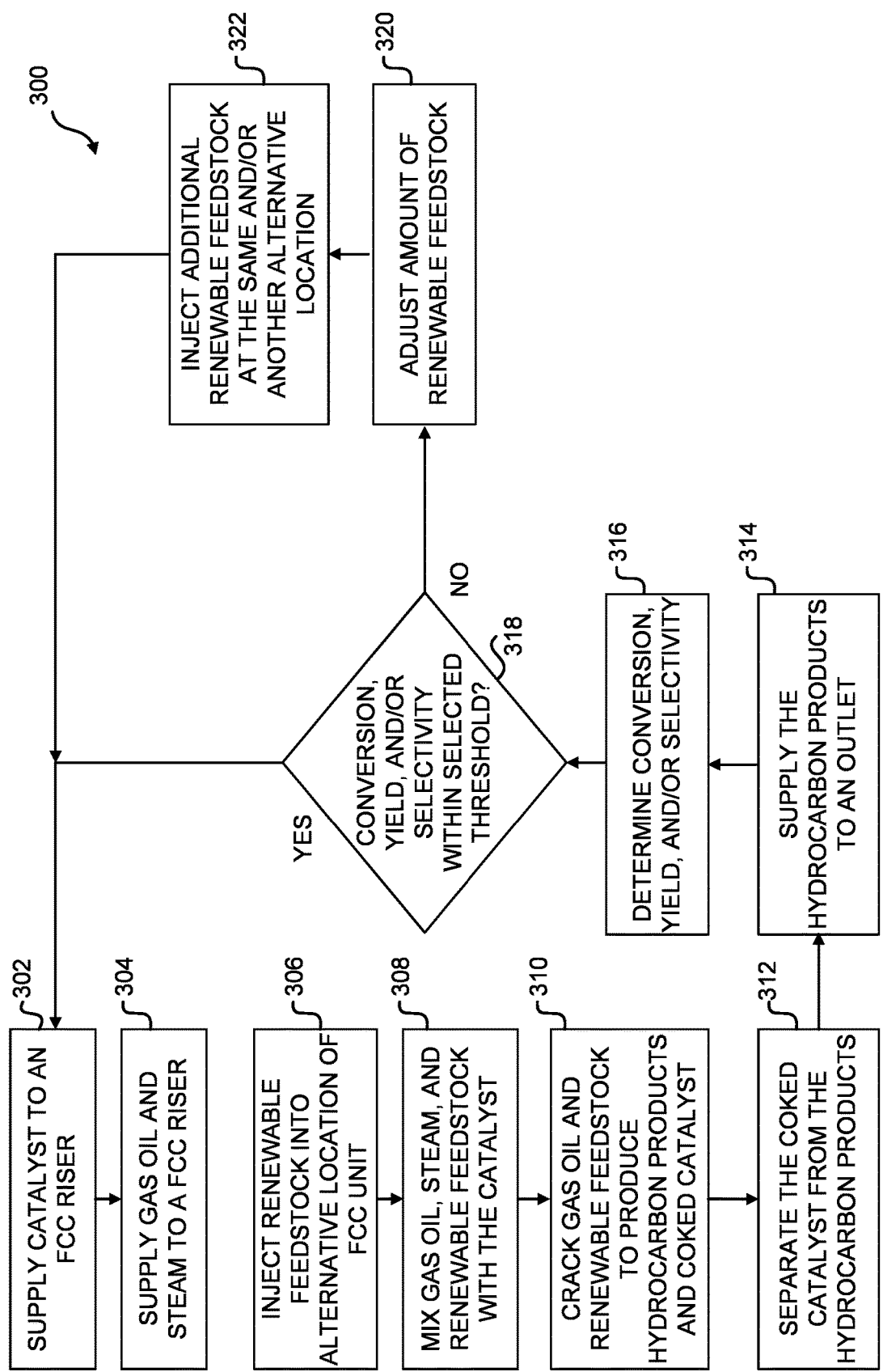

FIG. 3 is another block diagram of a method for processing of hydrocarbons in a FCC unit by introduction of a renewable feedstock into the FCC reactor, according to an embodiment of the disclosure.

Figure 4:
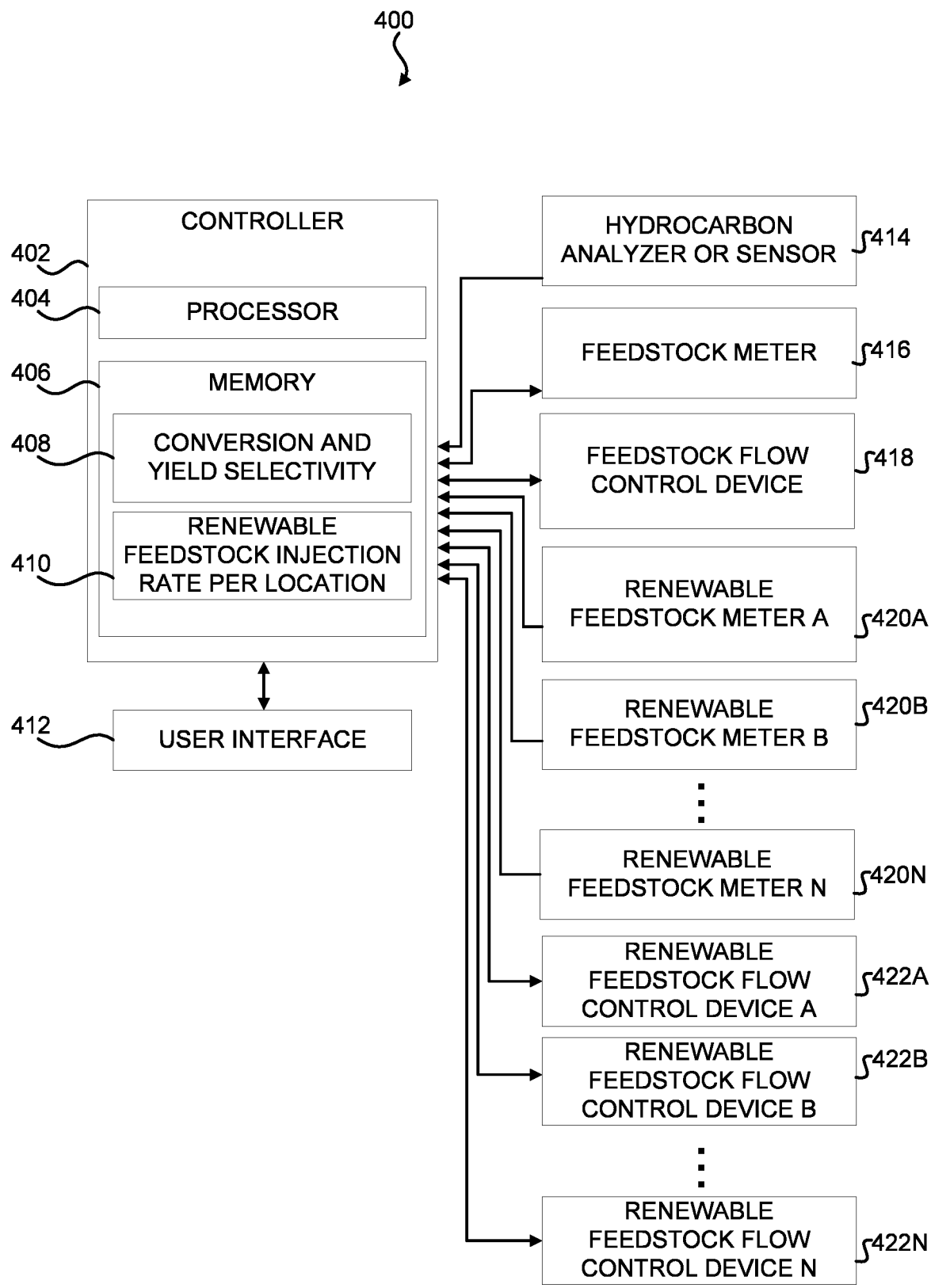

FIG. 4 is a simplified diagram illustrating a control system for managing the processing of hydrocarbons, according to an embodiment of the disclosure.

DETAILED DESCRIPTION

The disclosure now will be described more fully hereinafter with reference to specific embodiments and particularly to the various drawings provided herewith. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a," "an," "the," include plural referents unless the context clearly dictates otherwise.

Biomass includes any renewable source, but does not include oil, natural gas, and/or petroleum. Biomass thus may include wood, paper, crops, animal and plant fats, triglycerides, biological waste, algae, or mixtures of these biological materials. Biomass-derived pyrolysis oil may be a complex mixture of several organic compounds, such as lignin fragments, aldehydes, carboxylic acids, carbohydrates, phenols, furfurals, alcohols, and ketones, derived from Rapid Thermal Processing (RTP) of biomass feedstocks. In some embodiments, the RTP of biomass produces the pyrolysis oil that can be utilized as a FCC feedstock additive to debottleneck refinery.

Renewable feed or feedstock (feed and feedstock being used interchangeably) includes plastic-derived pyrolysis oil, plastic-based oil or plastic-based hydrocarbons refined via other methods (for example, the other methods including, but not limited to, hydrothermal processing, liquefaction, gasification, catalytic degradation, and/or other methods suitable for generating oil or another fluid from plastic, as will be understood by one skilled in the art), biomass-derived pyrolysis oil, municipal waste-derived pyrolysis oil, vegetable based feedstock, animal fat feedstock, algae oil, sugar-derived hydrocarbons, or carbohydrate-derived hydrocarbons.

The FCC units may include "stacked" and "side-by-side" reactors, as well as other configurations. In a stacked reactor, the FCC reactor and the FCC regenerator may be contained in a single vessel with the FCC reactor above the FCC regenerator. The side-by-side reactor includes a separate FCC reactor and FCC regenerator, in other words, a side-by-side reactor may include two separate vessels, often positioned side by side.

In certain embodiments of the FCC unit, a gas oil stream and steam may be supplied to a riser of the FCC unit. In another embodiment, rather than or in addition to gas oil, a renewable feedstock may be supplied to the riser of the FCC unit. In the riser, the gas oil (and/or renewable feedstock, in some embodiments) and steam are brought into contact with the catalyst for catalytic cracking and production or generation of FCC products. The resulting mixture may continue upwardly through an upper portion of the riser. Renewable feedstock (or, if renewable feedstock is supplied to the riser, an additional renewable feedstock) may be introduced into the FCC unit at one or more alternative locations of the FCC unit and/or, in some embodiments, with the gas oil. For example, the renewable feedstock may be injected separate from the gas oil, with the steam (and/or with other steam injected at different locations and/or for different purposes), at a dedicated nozzle on the riser, in a regenerator, and/or at a dedicated nozzle positioned in another or alternative location of the FCC unit (such as, the catalyst bed and/or a stripping zone). In embodiments, the alternative locations may include or comprise one or more of injection points separate from the gas oil injection point, at a FCC reactor catalyst bed, at an FCC catalyst stripper, at a nozzle located above or downstream of a gas oil injection point, at a nozzle below or upstream of the gas oil injection point, and/or at various points where steam is introduced into the FCC unit (for example, the renewable feedstock may be injected along with stripping steam, pre-stripping steam, or fluffing steam). The renewable feedstock may be injected into the FCC unit at a point where the catalyst within the FCC unit is at a density of about 20 lbs/ft$^3$ to about 35 lbs/ft$^3$, about 20 lbs/ft$^3$ to about 40 lbs/ft$^3$, or about 30 lbs/ft$^3$. One or more different renewable feedstock may be injected at one or more of the different alternative locations. For example, a first type of renewable feedstock (for example, plastic-derived pyrolysis oil) may be injected with the gas oil, while a second type of renewable feedstock (for example, biomass-derived pyrolysis feedstock) may be injected in the stripping zone of the FCC unit. The renewable feedstock may also be cracked with the gas oil and may increase conversion and selected yields (for example, propylene, plastic precursors, naphtha, LPG yields, and/or other feedstock or product yields). As noted, one of the one or more alternative locations may include or comprise one or more locations of the regenerator. The renewable feedstock may be injected into the regenerator via one or more of the alternative locations. The renewable feedstock may be injected into the regenerator to control temperature within the reactor and/or the heat-balance of the FCC unit.

The FCC unit may further include a reactor in communication with the riser for continuing production or generation of FCC products and then separating the FCC products from the coked FCC catalyst. During catalytic cracking, heavy material, known as coke, may be deposited onto the catalyst. The amount of coke deposited onto the catalyst (identified as, for example, a mass or weight of coked catalyst) in relation to a starting mass or weight of catalyst may be referred to as coke yield. Further, the coke yield per catalyst to oil (cat/oil) ratio or weight percentage may define a delta coke. In other words, delta coke may be an amount that indicates the amount of coke deposited onto catalyst (coke yield) in relation to a cat/oil ratio. In another embodiment, the delta coke may be defined by the mass or weight of the coked catalyst subtracted by the mass or weight of regenerated catalyst (in other words, the difference in mass or weight of the coked catalyst and the regenerated catalyst.

For example, polyethylene or polypropylene based pyrolysis oil may be injected into the reactor of the FCC unit. In such examples, depending on the quality of the polyethylene or polypropylene based pyrolysis oil (in other words, the amount of contaminants in the polyethylene or polypropylene based pyrolysis oil) the delta coke may decrease or may not change in relation to delta coke levels prior to introduction of the polyethylene or polypropylene based pyrolysis oil, and, in some embodiments, the delta coke may even increase (for example, injection of the polyethylene or polypropylene based pyrolysis oil into the stripper may increase delta coke.

In another example, a renewable feedstock may be added to the regenerator. Such an addition may increase the temperature within the regenerator. Further, due to the increased temperature more coke may be burned from the coked catalyst, as such, injection of renewable feedstock into the regenerator may increase the difference between the mass of coked catalyst entering the regenerator compared to the mass of regenerated catalyst leaving the regenerator, thus increasing the delta coke. In yet another example, the injection of the renewable feedstock into the regenerator may not change delta coke.

The depositing of coke onto the catalyst may reduce catalytic activity of the catalyst. As such, regeneration is desired so the catalyst may be reused. In certain embodiments, the FCC reactor may be equipped with one or more cyclones. Most, substantially all, or a portion of the coked FCC catalyst may be transported to one or more cyclones in the reactor, where the coked FCC catalyst may be separated from the FCC hydrocarbon products.

The FCC hydrocarbon products may be transported into a fractionation or distillation zone downstream of the FCC reactor. A portion of the FCC hydrocarbon products may be analyzed or characteristics determined by a sensor at the outlet of the FCC unit, such as, prior to transportation to a fractionation or distillation zone. Based on the determined characteristics and/or yield of the FCC hydrocarbon products, the amount, type, and/or injection point of the one or more renewable feedstock may be adjusted (for example, via a controller or other computing device). In certain embodiments, the coked FCC catalyst with the adsorbed or entrained hydrocarbons may be passed or transported through a stripping zone (and/or, in some embodiments, renewable feedstock may be injected into the stripping zone). Stripping gas, such as steam (and, in some embodiments, including additional renewable feedstock), may enter a lower portion of the stripping zone and may rise counter-current to a downward flow of catalyst through the stripping zone, thereby removing adsorbed and entrained hydrocarbons from the coked FCC catalyst which flow upwardly through and are ultimately recovered with the steam by the one or more cyclones. The FCC unit may further include a regenerator in communication with the FCC reactor, either directly or through the stripping zone, and configured to receive a portion of the coked FCC catalyst. After separation of the FCC products from the coked FCC catalyst, regeneration may be accomplished by burning off the coke from the coked FCC catalyst which restores the catalyst activity of the FCC catalyst. The regenerator may be equipped with inlets to supply oxygen and/or air (and, in some embodiments, renewable feedstock) to the coked FCC catalyst. The regenerator may be fed with the oxygen and/or air (and, in some embodiments, the renewable feedstock in any ratio) to the coked FCC catalyst by changing the flow rate into the regenerator. The coke in the coked FCC catalyst (and in some embodiments, renewable feedstock) may be oxidized by the oxygen to produce the regenerated catalyst.

In an embodiment, the oxygen may be provided or supplied separate from and/or with ambient and/or atmospheric air. Ambient and/or atmospheric air may include varying amounts of nitrogen, oxygen, and/or other gases (such as, argon, carbon dioxide, water vapor, and/or other small or trace amounts of other gases), as will be understood by one skilled in the art. Further, the ambient and/or atmospheric air may include about 78% nitrogen, about 21% oxygen, and about 1% of other gases (for example, about 0.9% argon, about 0.05% carbon dioxide, and other small or trace amounts of gases including, but not limited to, water vapor, neon, helium, methane, and/or krypton, as will be understood by one skilled in the art). As noted, oxygen may be supplied to the regenerator (for example, about 100% oxygen). In an embodiment, additional oxygen may be mixed with air (such as, ambient and/or atmospheric air) in varying amounts and supplied to the regenerator. For example, the mixture of oxygen and air may include or comprise about 70% nitrogen, about 29% oxygen, and/or other gases; about 60% nitrogen, about 39% oxygen, and/or other gases; about 50% nitrogen, about 49% oxygen, and/or other gases; about 40% nitrogen, about 59% oxygen, and/or other gases; about 30% nitrogen, about 69% oxygen, and/or other gases; 20% nitrogen, about 79%, and/or other gases; about 20% nitrogen, about 79%, and/or other gases; about 10% nitrogen, about 89% oxygen, and/or other gases; about 99% oxygen and/or other gases (such as, a mixture comprised of about 1% total of nitrogen, argon, carbon dioxide, water vapor, and/or other gases, as will be understood by one skilled in the art); and/or other varying percentages of nitrogen, oxygen, and/or other gases. In another embodiment, the additional oxygen may be supplied to the regenerator separate from the air (for example, via another injection point or location). In an embodiment, the amount of air and/or oxygen injected or supplied to the regenerator may be controlled by a controller and/or flow control devices. The amount of air and/or oxygen (in addition to or rather than adjustment of renewable feedstock injected into or supplied to the regenerator and/or reactor) may be varied based on the temperature within the regenerator (for example, the temperature which may indicate the amount of coke on the coked catalyst that is combusted).

The regenerator may be operated at temperatures in the range of about 1000° F. (about 538° C.) to 1600° F. (about 871° C.), of about 1000° F. (about 538° C.) to about 1500° F. (about 815° C.), of about 1100° F. (about 593° C.) to about 1450° F. (about 788° C.), at about 1250° F. (about 677° C.) to about 1400° F. (about 760° C.), or about 1300° F. (about 704° C.) to achieve adequate combustion while keeping catalyst temperature below those temperatures at which significant catalyst degradation can occur and/or above a temperature such that cracking in the reactor may be efficient. In one or more other embodiments, the temperature in the regenerator may not exceed greater than or may be held at about 1450° F. (about 788° C.), about 1400° F. (about 760° C.), about 1350° F. (about 732° C.), about 1300° F. (about 704° C.), about 1250° F. (about 677° C.), about 1200° F. (about 649° C.), about 1150° F. (about 621° C.), about 1100° F. (about 593° C.), about 1050° F. (about 565° C.), and/or about 1000° F. (about 538° C.). The temperature at which significant catalyst degradation may occur may be based on a number of variables, such as the temperature and/or water content within the FCC unit (such characteristics may be monitored via one or more sensors and/or probes), among other factors. In embodiments, this processing of the renewable feedstock in the regenerator may alleviate FCC processing constraints and optimizes refinery profitability. The renewable feedstock, when utilized as a FCC feedstock additive, may be injected in low concentrations into the regenerator and/or other alternative locations of the FCC unit. While crackability of some renewable feedstock, such as biomass derived pyoil, is poor (high levels of coke precursors/aromatics), which results in lower FCC conversion, the impact on heat balance is significant.

In certain embodiments, renewable feedstock, particularly biomass-derived pyrolysis oil, may have an effective hydrogen index of less than 1.5. In other embodiments, the renewable feedstock may have an effective hydrogen higher than 1.5, for example, plastic pyoil may exhibit a higher hydrogen index, such as 2 or even greater. The hydrogen index of the renewable feedstock or FCC feedstock additive may be determined via the following equation:

$$\frac{H - 20 - 3N - 2S}{C}$$

where H is hydrogen atoms, C is carbon atoms, O is oxygen atoms, N is nitrogen atoms, and S is sulfur atoms. In such examples, oxygenates having a hydrogen index of less than 1 cause excessive amounts of coke to be produced. Additionally, FCC feedstock additives with a low hydrogen content may also change or affect overall FCC yield selectivities. The FCC feedstock additive may be a net hydrogen receptor inside the FCC unit (lower hydrogen content than fresh feed). Depending on the incremental yields attributed to this FCC feedstock additive, additional economic value (such as via renewable identification numbers, low carbon fuel standard credits, and/or other renewable/recycling programs) may be applicable. Utilizing this renewable FCC feedstock additive can sustainably debottleneck FCC operation/constraints and optimize refinery profitability. Additionally, FCC feedstock additives with a high hydrogen content may increase yields from an FCC unit. Thus, such feedstock additives may be injected at varying locations throughout the FCC unit to increase yields, in addition to balancing heat.

Other renewable feedstock, used as FCC feedstock additives, may include or have a different effective hydrogen index than that of the biomass-derived pyrolysis oil, as noted herein. These other renewable feedstock may include one or more of plastic-derived pyrolysis oil, plastic-based oil or plastic-based hydrocarbons refined via other methods (for example, the other methods including, but not limited to, hydrothermal processing, liquefaction, gasification, catalytic degradation, and/or other methods suitable for generating oil or another fluid from plastic, as will be understood by one skilled in the art), municipal waste-derived pyrolysis oil, vegetable based feedstock, animal fat feedstock, algae oil, sugar-derived hydrocarbons, or carbohydrate-derived hydrocarbons. During cracking, one or more of these other renewable feedstock and/or the biomass-derived pyrolysis oil may be selected to produce or increase selected yields. For example, one or more of the renewable feedstock may be selected to increase LPG yield, increase propylene production, increase plastic pre-cursor yields, and/or increase yields of other feedstock and/or products. Selection of the renewable feedstock may further cause a decrease in coke yield when, for example, the renewable feedstock is injected into the regenerator depending on a number of factors, such as the quality of the renewable feedstock. This selection of introduction of the renewable feedstock to the various alternate locations, such as alternate locations of the reactor and/or regenerator, of the FCC unit offers selected yields improvements, such as an increase in yield of various products and/or feedstock, further optimization of energy consumption, heat balance, and/or reduced coke yield.

The addition of renewable feedstock directly into the FCC unit (such as, at one or more locations, including various alternate locations) may, as noted, enhance cracking operations and/or yield of the FCC unit. For example, the renewable feedstock may increase conversion and LPG yield of the cracking operation. In another example, the renewable feedstock, when injected into the reactor, may reduce delta coke (and, in some embodiments, increase the delta coke or maintain a current delta coke). The renewable feedstock may increase residence time and promote higher degrees of cracking the gas oil and the one or more renewable feedstock into lighter hydrocarbon products (such as, naphtha or liquefied petroleum gas (LPG)), while reducing or lowering delta coke (when injected into the reactor). The renewable feedstock may increase delta coke, for example, when injected into the regenerator (and/or, in some embodiments, alternative locations in the reactor). In yet another embodiment, delta coke may be balanced (or at similar levels when compared to a scenario where renewable feedstock is not injected into the FCC unit) when renewable feedstock is injected into the reactor and regenerator.

The renewable feedstock may comprise one or more of plastic-derived pyrolysis oil, plastic-based oil or plastic-based hydrocarbons refined via other methods (for example, the other methods including, but not limited to, hydrothermal processing, liquefaction, gasification, catalytic degradation, and/or other methods suitable for generating oil or another fluid from plastic, as will be understood by one skilled in the art), biomass-derived pyrolysis oil, municipal waste-derived pyrolysis oil, vegetable based feedstock, animal fat feedstock, algae oil, sugar-derived hydrocarbons, or carbohydrate-derived hydrocarbons. The amount of renewable feedstock injected into or supplied to the FCC unit may be about 1% to about 99% volume percent of the gas oil introduced into the riser of the FCC unit. The amount of renewable feedstock may include a blend of pyrolysis oil and wax. The blend may comprise about 60% to about 100% pyrolysis oil and about 40% to about 0% wax or, in an embodiment, about 70% pyrolysis oil and about 30% wax.

FIG. 1A is a schematic diagram of a non-limiting, FCC system 100 according to one or more embodiments of the disclosure. A gas oil or feed stream 124 and steam may be supplied to a riser 106 of a FCC system 100 via an inlet, conduit, pipe, or pipeline (such as, conduit 102 and conduit 103, respectively). The feed stream may include gas oil, as noted. In other embodiments, the feed stream may include or may be about 1% to about 100% renewable feedstock. Appropriate FCC catalysts 128 may be supplied via a catalyst stream via an inlet, conduit, pipe, or pipeline (for example, inlet 104), as will be understood by one skilled in the art. In the riser 106, the gas oil or feed stream 124 and steam may be brought into contact with the FCC catalyst 128 or catalyst stream for catalytic cracking and production or generation of FCC products.

In certain embodiments, the gas oil or feed stream 124 can contain one or more of other feeds, such as renewable feedstock, conventional FCC feed streams, and decant oil. The riser 106 may be operated under cracking reaction pressure and temperature conditions to facilitate mixing and catalytic cracking of the gas oil stream in presence of the steam and the FCC catalyst to form a plurality of FCC products and coked FCC catalyst. The reaction temperature, feed stream rates, feed residence time, gas oil/steam FCC feed concentrations, and FCC catalyst loadings may be modified to obtain maximum fuel range products. The resulting mixture continues upwardly to the FCC reactor 107 through an upper portion of the riser 106. The FCC reactor 107 may contain a FCC reaction zone 108 connected to and in fluid communication with the upper portion of the riser 106 and operated to continue the cracking of the gas oil stream in presence of the steam and the FCC catalyst to generate, produce, or yield more of the plurality of FCC products and more of the coked FCC catalyst. The FCC reactor 107 may contain a separation zone 109 to separate the plurality of FCC products from the coked FCC catalyst. In certain embodiments, the separation zone 109 may contain one or more cyclones 149 to separate the coked FCC catalyst from the plurality of FCC products. The FCC reactor 107 may also contain an outlet 110 to transport the plurality of FCC products from the separation zone 109 to a fractionation zone to separate the plurality of FCC products into one or more of propylene, isobutene, butylenes, gasoline, distillate, diesel fuel or heating oil, slurry oil and wet gas.

The FCC reactor 107 and/or the riser 106 may include a number of different inlets. For example, the riser 106 may include an inlet 142 and an inlet 150. Inlet 142 and an inlet 150 may be dedicated inlets to enable injection of an amount of renewable feedstock into the riser 106. Inlet 142 may be positioned below or upstream of the conduit 102. Inlet 150 may be positioned above or downstream of the conduit 102. In an embodiment, the riser may include one or more of inlet 142 or an inlet 150. Further, renewable feedstock may be injected with the FCC catalyst 128, with the gas oil or feed stream 124 (such as, via the conduit 102), with the stripping steam 126 (such as, via conduit 103), and/or with a fluffing steam 156 (such as, via conduit 154). Further, the renewable feedstock may be injected into the other zones of the FCC reactor 107, such as with a pre-stripping steam 164 (such as, via conduit 162) and/or via another dedicated inlet 166 (for example, renewable feedstock 168). As noted, one or all of these inlets or conduits may be utilized to inject an amount or portion of renewable feedstock. The renewable feedstock may be cracked or a portion of the renewable feedstock may be cracked along with the gas oil. Any remaining renewable feedstock may be transported, along with spent catalyst 140 to the regenerator 116. In such embodiments, the remaining renewable feedstock may be deposited onto the spent catalyst, along with coke, for example, when the renewable feedstock polymerizes about, hardens onto, or otherwise becomes attached to the spent catalyst the spent catalyst 140. Flow control devices (such as, valves and/or pumps, among other devices configured to control flow) may be positioned along or on each of the conduits or inlets to control an amount of renewable feedstock injected into the FCC reactor 107. Further, the same or different types of renewable feedstock may be injected or supplied at each of a plurality of the conduits or inlets. The conduits or inlets, as noted, may be dedicated inlets for renewable feedstock. The dedicated inlets may be retro-fitted, added to, and/or installed on the FCC reactor 107 or FCC unit.

In certain embodiments, the coked FCC catalyst 128 with the adsorbed or entrained hydrocarbons may be passed into a stripping zone. Stripping gas, such as steam, may enter or may be injected into a lower portion of the stripping zone. The stripping gas may rise counter-current to a downward flow of catalyst through the stripping zone, thereby removing adsorbed and entrained hydrocarbons from the coked FCC catalyst which flow upwardly through and are ultimately recovered with the steam by the one or more cyclones 149. The FCC system 100 may further include a regenerator 116 in fluid communication with the FCC reactor 107 (such as, via a conduit, pipe, inlet/outlet, or pipeline), either directly or through the stripping zone, and configured to receive a portion of the coked FCC catalyst via a spent catalyst stream (for example, via conduit 114). A valve 138 may be positioned on the conduit 114 to control the amount of the coked FCC catalyst flowing to the regenerator 116. After separation of the FCC products from the coked FCC catalyst, regeneration may be accomplished by burning off the coke from the coked FCC catalyst, which restores the catalyst activity of the FCC catalyst. The regenerator 116 may be equipped with an air inlet 117 to supply air 130 and a renewable feedstock inlet 118 to supply renewable feedstock 132, for example, plastic-derived or biomass-derived pyrolysis oil, to the coked FCC catalyst. The regenerator 116 may be fed with air 130 and/or oxygen and the renewable feedstock in any ratio to the coked FCC catalyst by changing the flow rate of air supplied via the air inlet 117 and the renewable feedstock 132 supplied via the renewable feedstock inlet 118 into the regenerator 116. The renewable feedstock 132 and the coke in the coked FCC catalyst may be oxidized by oxygen in the air to produce the regenerated catalyst. Such a reaction may be exothermic as a large amount of heat is released from the oxidation. The gaseous products of coke oxidation, which may be referred to as flue gas, may be collected, such as via one or more cyclones 147, and exit the regenerator 116 via the exit stream 122. The balance of the heat may cause the regenerator to produce the regenerated catalyst. The regenerated catalyst, in addition to providing a catalytic function, may act as a vehicle for the transfer of heat from the regenerator 116 to the FCC riser 106. The regenerated catalyst may be transported from the regenerator 116 via a catalyst outlet stream to the FCC riser 106 (for example, via a conduit 120). A valve 134 may be positioned on the conduit 120 to control the amount of the regenerated catalyst flowing to the riser 106. In an embodiment, the regenerated catalyst from the catalyst outlet stream may be mixed with a small amount of fresh catalyst (such as, in relation to the amount of regenerated catalyst) and supplied to the riser 106 of a FCC system 100 via the catalyst stream (for example, inlet 104).

In certain embodiments, the regenerator 116 of an existing FCC unit may be adapted or retro-fitted to add an element to allow for the introduction of the renewable feedstock to the regenerator. For example, this element can be an installed independent conduit, pipe, or pipeline for introducing the renewable feedstock (for example, renewable feedstock inlet 118). The flow through this element can be initiated, modified, or stopped by an independent control system or by a control system (such as a controller) for the regenerator or the FCC unit. Various control designs and/or schemes may also be suitable for use in introduction of the renewable feedstock to the regenerator of an existing FCC unit. Various configurations and arrangements of FCC reactor and the regenerator, including the positioning of various sections and/or components therein, may vary as will be understood by a person skilled in the art.

In another embodiment, the FCC system 100 may include a controller or control system (such as controller 123 in FIG. 1B or controller 402 in FIG. 4) and various sensors, probes, analyzers, and/or control valves (such as, valve 134 and/or valve 138) positioned throughout the FCC system 100 and in signal communication with the controller or control system. The controller or control system may receive and send information, data, and/or instructions to and from, respectively, the various sensors, probes, analyzers, and/or control valves. In such examples, the controller or control system may receive some characteristic regarding one or more different parts or products of the FCC system 100 from the sensors, analyzers, and/or probes (for example, temperature within the regenerator 116, riser 106, a reactor or FCC reactor 107, and/or composition and/or yield of FCC hydrocarbon products) and, based on those characteristics and one or more preselected thresholds (such as, a preselected temperature range within the regenerator 116, riser 106, and/or FCC reactor 107), adjust flow and/or amount of one or more materials or fluids flowing into or supplied to the regenerator 116, riser 106, and/or FCC reactor 107 (such as, gas oil, pyoil, renewable feedstock, fresh catalyst, regenerated catalyst, air, and/or steam).

FIG. 1B a schematic diagram of a non-limiting, FCC system 100 according to one or more embodiments of the disclosure. The FCC system 100, as noted, may include a reactor or FCC reactor 107 and regenerator 116. Those components (and in another embodiment, other components) may be a part of an energy envelope 180 (for example, the components may utilize heat from one another to ensure thermally stable processes with minimal external heating, such as from natural gas 196 and/or electricity 197). The FCC system 100 may include a control valve 174 to control the amount or flow of FCC hydrocarbon products flowing to a fractionation or distillation tower 182. The fractionation or distillation tower 182 may produce an off gas 190, an LPG 191 (which may be processed further via an alkylation unit 184 to produce an alkylate 192), a gasoline 193 (after passing a product through a hydrotreater 186), a diesel 194 (after passing a product through a hydrotreater 188), and/or a slurry 195.

Further, the FCC system 100, as noted, may include a controller 123 and one or more sensors, analyzers, and/or control valves positioned throughout. For example, the FCC system 100 may include a sensor 135 positioned along the riser. The sensor 135 may measure one or more of the pressure, temperature, and/or other characteristics of the materials flowing into the riser (such as, regenerated catalyst, renewable feedstock, gas oil, and/or other additives or feedstock) and provide the measurement, periodically or continuously, to the controller 123. The FCC system 100 may include a sensor 137 to measure one or more of the pressure, temperature, and/or other characteristics of the coked catalyst flowing from the FCC reactor 107 to the regenerator 116 and provide the measurement, periodically or continuously, to the controller 123. The FCC system 100 may include a sensor 145 and/or analyzer to measure one or more of the pressure, temperature, and/or other characteristics of the materials within one or more different locations of the FCC reactor 107, as well as provide the measurement, periodically or continuously, to the controller 123. The FCC system 100 may include a sensor 143 to measure one or more of the pressure, temperature, and/or other characteristics of the products produced in the FCC reactor 107 and provide the measurement, periodically or continuously, to the controller 123. The FCC system 100 may include a sensor 133 to measure one or more of the pressure, temperature, and/or other characteristics of the regenerated catalyst flowing from the regenerator 116 to the riser and/or FCC reactor 107 and provide the measurement, periodically or continuously, to the controller 123. Finally, the FCC system 100 may include a sensor 141 and/or analyzer to measure one or more of the pressure, temperature, and/or other characteristics of the materials within one or more different locations of the FCC reactor 107, as well as provide the measurement, periodically or continuously, to the controller 123.

The FCC system 100 may include one or more control valves (for example, control valve 127, control valve 129, control valve 131, and control valve 151) and/or, in other embodiments, other flow control devices (for example, a pump). Each control valve (and/or other flow control devices) may adjust the flow of a fluid or material based on a preselected threshold and a signal received from the controller 123. For example, control valve 129 and control valve 131 may adjust the amount of renewable feedstock and air, respectively, introduced into (in other words, the flow rate of the renewable feedstock and air, respectively) the regenerator 116. The controller 123 may determine the flow rate based on the temperature within regenerator 116, the temperature of regenerated catalyst flowing from the regenerator 116, the temperature within the FCC reactor 107, the temperature of coked catalyst flowing from the FCC reactor 107, the yield and/or amount of products produced, the pressure within the regenerator 116, and/or the temperature within the riser, among other factors. For example, if the temperature within the FCC reactor 107 is below a specified threshold and/or if the yield and/or amount of products produced or flowing from the FCC reactor 107 is below another specified threshold, then the controller 123 may increase the amount of renewable feedstock flowing into the regenerator 116 (or into other locations). The controller 123 may transmit a signal indicative of the flow rate to the corresponding control valve, causing the corresponding control valve to adjust such that the indicated flow rate is reached. Further, based on such factors, the amount of regenerated catalyst flowing to the regenerator 116 from the FCC reactor 107 may be adjusted via control valve 125. Finally, the control valve 127 may control the amount of regenerate catalyst flowing from the regenerator 116 to FCC reactor 107 based on the temperature within regenerator 116, the temperature of regenerated catalyst flowing from the regenerator 116, the temperature within the FCC reactor 107, the temperature of coked catalyst flowing from the FCC reactor 107, the pressure within the regenerator 116 and/or FCC reactor 107, the yield and/or amount of products produced, and/or the temperature within the riser, among other factors. Other factors may be utilized to determine the flow rates described herein, such as pressure within other components and/or current flow rates, as well as analysis of the materials described herein (such as products and/or byproducts of the reactor and/or regenerator).

In another embodiment, renewable feedstock may be introduced into the riser of the FCC reactor 107 via the same inlet as typical feed (such as, gas oil) and/or via a separate and/or dedicated inlet. A control valve 151 may be positioned along such an inlet to adjust the amount of renewable feedstock introduced into the FCC reactor 107. The amount of renewable feedstock to be introduced into the FCC reactor 107, determined by the controller 123, may be based on one or more of the temperature and/or pressure within the FCC reactor 107, the temperature and/or pressure within the regenerator 116, the composition of the products produced by the FCC reactor 107, one or more selected product yields from the FCC reactor 107, and/or the temperature of the products flowing from the FCC reactor 107, among other factors. Other control valves may be positioned along inlets associated with other alternative locations for introduction of renewable feedstock.

FIG. 2 is a block diagram of a method 200 for enhancing the processing of hydrocarbons in a FCC unit by introduction of a renewable feedstock into the FCC unit. In an embodiment, the actions of method 200 may be completed within a control system (such as controller 402). Specifically, method 200 may be included in one or more programs, protocols, or instructions loaded into a memory of the control system and executed on a processor or one or more processors of the control system. The order in which the operations are described is not intended to be construed as a limitation, and any number of the described blocks may be combined in any order and/or in parallel to implement the methods.

At block 202, an amount of gas oil and steam may be introduced to into a riser of a FCC unit. The gas oil can be one or more of the following feeds: atmospheric and vacuum gas oil, light and heavy coker gas oil, hydrocracked residue, atmospheric residue, or deasphalted oil. The hydrocarbons in the gas oil feed includes paraffins and cycloparaffins, aromatic hydrocarbons with a different number of aromatic rings, and resins and asphaltenes. At block 204, the gas oil and the steam may be mixed with a FCC catalyst that is fluidized in the riser. At block 206, a renewable feedstock may be injected into the FCC unit at one or more alternative locations of the FCC unit at varying times (for example, after gas oil enters the FCC unit, at a point during a cracking operation, or at some point after cracking occurs). In some embodiments, the renewable feedstock may mix with the gas oil and steam. At block 208, the gas oil and/or renewable feedstock are subject to catalytic cracking of the higher molecular weight hydrocarbons into one or more FCC products. The cracking of the gas oil and renewable feedstock may cause one or more surfaces of the catalyst to be at least partially covered by coke, thus producing a coked FCC catalyst. At block 210, the coked FCC catalyst is separated from the one or more FCC products in one or more cyclones of the FCC unit and, at block 212, the hydrocarbon products are passed to an outlet of the FCC unit from the one or more cyclones or from another location of the FCC unit. In another embodiment, the renewable feedstock can be introduced into a bed of coked FCC catalyst positioned inside the regenerator (or in other locations of the regenerator), rather than or in addition to the renewable feedstock being injected into the reactor. The renewable feedstock injected into the regenerator may be utilized to manage heat within the reactor by increasing the temperature of regenerated catalyst.

In some embodiments, the amount of renewable feedstock injected into the FCC unit may vary based on hydrocarbon product specifications (for example, selected yields for one or more products or feedstock). As such, during a FCC operation, the resulting hydrocarbon product may be analyzed or characteristics may be determined via a sensor or analyzer. Based on those characteristics, the amount, type, and injection location of the renewable feedstock may vary. Such adjustment may occur continuously or substantially continuously throughout a FCC or cracking operation.

FIG. 3 is a block diagram of a method 300 for enhancing the processing of hydrocarbons in a FCC unit by introduction of a renewable feedstock into the FCC unit. In an embodiment, the actions of method 300 may be completed within a control system (such as, such as controller 402). Specifically, method 300 may be included in one or more programs, protocols, or instructions loaded into a memory of the control system and executed on a processor or one or more processors of the control system. The order in which the operations are described is not intended to be construed as a limitation, and any number of the described blocks may be combined in any order and/or in parallel to implement the methods.

At block 302, during a cracking operation or upon an initiation of a cracking operation, an amount of catalyst may be supplied to a riser or FCC riser of a FCC unit. The catalyst (also referred to as a FCC catalyst) may be comprised of a zeolite and/or other components (such as, a matrix, binder, and/or filler), as will be understood by one skilled in the art. The amount of catalyst supplied to the riser of the FCC unit may vary over time. For example, as catalyst within the FCC unit is utilized in a cracking operation, the catalyst may attract or become coked (for example, coke accumulates on the catalyst). The coked or spent catalyst may be transferred from the FCC unit and new or fresh and/or regenerated catalyst may be supplied the riser of the FCC unit. The amount of catalyst supplied to the FCC unit may be adjusted based on the current amount of catalyst within the FCC unit. In such examples, a control system (such as, controller 402) may determine the current amount of catalyst in the FCC unit based on the amount of catalyst transferred to a regenerator, the amount of catalyst supplied to the FCC unit, the composition of hydrocarbon products produced by the FCC unit, and/or the yield of one or more selected hydrocarbon products produced by the FCC unit.

At block 304, a gas oil and steam may be supplied to the riser of the FCC unit. In an embodiment, the gas oil may be preheated prior to introduction or being supplied to the riser of the FCC unit. The temperature within the FCC unit (for example, based on the temperature of the steam, gas oil, and/or catalyst) may be within the range of about 650° F. (about 343° C.) to about 1050° F. (about 566° C.), or even higher, to perform a cracking operation based on the type of gas oil supplied to the FCC unit. Further, heat from regenerated catalyst may be utilized to increase temperature, as described herein and with further detail below.

At block 306, an amount of renewable feedstock may be injected into the riser or at another alternate location of the FCC unit. The renewable feedstock may mix with the gas oil and steam. In an embodiment, the renewable feedstock may be pre-heated prior to introduction into the FCC unit based on the temperature within the FCC unit.

At block 308 and as noted, the gas oil, renewable feedstock, and steam may mix with the catalyst in the riser of the FCC unit. At block 310, the gas oil and the renewable feedstock or a portion of the renewable feedstock may be cracked (for example, higher molecular weight hydrocarbons are converted or cracked to smaller vaporous molecules). Such a cracking operation may cause coke or carbonaceous material to form on the surface of the catalyst thereby forming a coked catalyst. The use of the renewable feedstock may reduce such coke formation, although some amount of coke may form. Forming of the coke on the catalyst may reduce the catalytic capability of the catalyst, thus, to utilize the catalyst in further operations or again, the coked catalyst may be passed through a regenerator.

At block 312, the coked catalyst (and, in some embodiments, an uncracked portion of the renewable feedstock) may be separated from the hydrocarbon or gas products formed via the cracking operation. Such separation may occur via one or more cyclones included in the reactor of the FCC unit. At block 314, the hydrocarbon products formed during cracking may be supplied to an outlet of the FCC unit. At block 316, the conversion and LPG yield of the cracking operation may be determined. An analyzer and/or sensor, in conjunction with a controller or other computing device, may determine the conversion, yield, and selectivity of the FCC unit output. In other words, the hydrocarbon product may be analyzed or characteristics of the hydrocarbon product may be sensed. Based on those characteristics, the conversion, yield, and selectivity may be determined. At block 318, the conversion, yield, and selectivity may be compared to one or more selected thresholds (for example, propylene yield and selectivity, and/or plastic precursor yield and selectivity). The selected threshold may be a value (such as an output or yield of a particular feedstock or product) at which the cracking operation is economically feasible. The selected threshold may be a value indicating a maximum or high operating efficiency of the FCC unit. In a further embodiment, the selected threshold may be a range of values.

If the conversion, yield, and selectivity is within the selected threshold, then method 300 may be executed again (or during a cracking operation). If the conversion and LPG yield is not within the selected threshold, then at block 320, the amount of renewable feedstock may be adjusted. Further, at block 322, the location of where the renewable feedstock or other renewable feedstock is injected into the FCC unit may be changed (for example, renewable feedstock may be injected into the FCC unit at the same and/or different alternative location of the FCC unit). In another embodiment, other factors may be considered when adjusting the amount and/or location of renewable feedstock injected into the FCC unit. For example, the temperature within the FCC unit, the pressure within the FCC unit, sulfur specifications (such as, how much sulfur may be in the hydrocarbon products), the type of gas oil being cracked, whether the cracking operation is using all renewable feedstock (such as, no gas oil is supplied to the FCC unit), and/or the type of renewable feedstock available.

FIG. 4 is a simplified diagram illustrating a system 400 for managing the processing of hydrocarbons, according to one or more embodiments disclosed herein. In an example, the control system may include a controller 402 or one or more controllers. Further, the controller 402 may be in signal communication with various other controllers throughout or external to a refinery. The controller 402 may be considered a supervisory controller. In another example, a supervisory controller may include the functionality of controller 402.

Each controller 402 described above and herein may include a machine-readable storage medium (such as, memory 406) and one or more processors (such as, processor 404). As used herein, a "machine-readable storage medium" may be any electronic, magnetic, optical, or other physical storage apparatus to contain or store information such as executable instructions, data, and the like. For example, any machine-readable storage medium described herein may be any of random access memory (RAM), volatile memory, non-volatile memory, flash memory, a storage drive (such as a hard drive), a solid state drive, any type of storage disc, and the like, or a combination thereof. The memory 406 may store or include instructions executable by the processor 404. As used herein, a "processor" may include, for example one processor or multiple processors included in a single device or distributed across multiple computing devices. The processor 404 may be at least one of a central processing unit (CPU), a semiconductor-based microprocessor, a graphics processing unit (GPU), a field-programmable gate array (FPGA) to retrieve and execute instructions, a real time processor (RTP), other electronic circuitry suitable for the retrieval and execution instructions stored on a machine-readable storage medium, or a combination thereof.

As used herein, "signal communication" refers to electric communication such as hard wiring two components together or wireless communication, as understood by those skilled in the art. For example, wireless communication may be Wi-Fi®, Bluetooth®, ZigBee, or forms of near field communications. In addition, signal communication may include one or more intermediate controllers or relays disposed between elements that are in signal communication with one another.

In an embodiment, the controller 402 may obtain the temperature at various points and/or locations or of materials in the system 400 or FCC unit. For example, a reactor temperature sensor or probe may provide, in real-time and/or continuously or at regular intervals, a signal to the controller 402 indicative of the temperature within the reactor and/or indicative of temperature of the materials within the reactor. In another example, a regenerator temperature sensor or probe may provide, in real-time and/or continuously or at regular intervals, a signal to the controller 402 indicative of the temperature within the regenerator and/or indicative of temperature of the materials within the reactor. Other temperatures sensors and/or probes may be positioned at varying locations throughout the system, including, but not limited to, at each inlet of the reactor, riser, and/or regenerator; at each outlet of the reactor, riser, and/or regenerator; and/or within a well or stand-pipe configured to store regenerated catalyst. Other sensors may be disposed throughout the system 400 to measure or indicate various other aspects or characteristic within the system, such as hydrocarbon analyzer or sensor 414 (for example, to measure the content of a hydrocarbon product produced by an FCC unit), a feedstock meter 416 (for example, to indicate a flow rate and/or amount of feedstock flowing to the riser), and/or one or more renewable feedstock meters 420A, 420B, and up to 420N (for example, to indicate a flow rate and/or amount of renewable feedstock flowing into various locations of the FCC unit). Other sensors or probes may measure or indicate pressure, gravity, API gravity, and/or other characteristics.

In an example, the sensors or probes positioned and/or disposed throughout the system 400 may be pressure transducers, flow meters, mass flow meters, Coriolis meters, other measurement sensors to determine a density, flow, temperature, or other variable as will be understood by those skilled in the art, or some combination thereof. In such examples, the sensors may measure the density of a fluid or material, the flow of the fluid or material, the temperature of the fluid or material, and/or the pressure within various locations of the system (such as, within the reactor, riser, and/or regenerator). In an embodiment, an analyzer may be utilized to measure or determine some characteristic of a fluid within or produced by the FCC unit. As noted above, the controller 402 may be in signal communication with the sensors, probes, analyzers, or meters. The controller 402 may poll or request data from the sensors and/or analyzers at various points or substantially continuously during a FCC, cracking, and/or regeneration operation.

In an embodiment, the system 400 may include one or more different flow control devices. For example, the system 400 may include a feedstock flow control device 418, one or more renewable feedstock flow control devices 422A, 422B, and up to 422N, and/or other flow control devices to control an amount of material or fluid flowing from one location to another. Each flow control device may include one or more of a pump, a meter (as described herein), a sensor or probe (as described herein), a valve (such as, a control valve, a slide valve, or another valve configured to control an amount of fluid or material flowing therethrough), and/or some combination thereof. In such examples, each component of the flow control device may be in signal communication with the controller 402. The flow control devices may allow for adjustment of the flow of the fluid or material based on various factors received by the controller 402.

The controller 402, according to an embodiment, may include instructions 408 to determine a conversion, yield, and selectivity of a FCC unit. The controller 402 may determine such values based on analysis of the hydrocarbons produced by the FCC unit, such as by a hydrocarbon analyzer or sensor 414, the amount of feedstock (such as, gas oil and/or renewable feedstock) supplied to the FCC unit, and/or the amount of catalyst flowing from the FCC unit (for example, coked catalyst). The controller 402 may take into consideration the amount of feedstock utilized, the amount of renewable feedstock utilized, and the amount of hydrocarbon products produced with the amount of feedstock and renewable feedstock. Other factors may be taken into consideration by the controller 402 such as temperature of the FCC unit, pressure within the FCC unit, and/or type of feedstock and/or renewable feedstock.

The controller 402, in another embodiment, may include instructions 410 to adjust an amount of renewable feedstock injected into the FCC unit per one or more locations. The controller 402 may determine such an adjustment based on the conversion, yield, and selectivity, among other factors. The controller 402 may adjust the renewable feedstock (such as, amount and/or injection location) based on other factors, as noted, such as temperature. To increase temperature, for example, the controller 402 may adjust an amount of renewable feedstock injected near where coked catalyst flows to the regenerator. Thus, renewable feedstock may flow to the regenerator and combustion of the renewable feedstock may cause an increase in temperature.

In another embodiment, the controller 402 may control flow rates of other materials or fluids, such as the amount of air introduced into the regenerator (for example, via an air flow control device), the amount of coked catalyst flowing into the regenerator (for example, via the coked catalyst flow control device), the amount of pyoil flowing into the regenerator or riser (for example, via the pyoil flow control device), and/or the amount of gas oil or feed flowing into the riser (for example, via the feedstock flow control device 418). Other factors, as noted, may be utilized in adjusting such flow rates, such as pressure, density, and/or temperature, among other factors (for example, for example, capacity of the reactor, riser, and/or well or stand-pipe).

In another embodiment, the controller 402 may comprise or include a first set of one or more inputs in signal communication with one or more sensors or analyzers (for example, hydrocarbon analyzer or sensor 414, feedstock meter 416, renewable feedstock meter 420A, 420B, and up to 420N, and/or another sensor or meter). The one or more sensors, analyzers, or meters may be positioned within or proximate to one or more of a regenerator, a riser of an FCC unit, a reactor of the FCC unit, and/or other conduits or pipe and/or inlets and/or outlets associated with the regenerator, the riser of the FCC unit, and/or the reactor of the FCC unit. The controller 402 may receive signals from the one or more sensors or analyzers indicative of a characteristic. The characteristic may comprise one or more of temperature, pressure, flow rate, composition, and/or yield or yield percentages. The controller 402 may comprise a first set of one or more inputs/outputs in signal communication with one or more flow control devices (for example, feedstock flow control device 418 and/or one or more renewable feedstock flow control devices 422A, 422B, and up to 422N) positioned on one or more inlets or outlets associated with the regenerator, the riser of the FCC unit, and/or the reactor of the FCC unit. The controller 402 may, in response to the characteristic from one of the one or more sensors being less than or greater than a preselected threshold (such as, a temperature, pressure, flow rate range, and/or yield, among other factors), adjust the one or more flow control devices via a signal indicating a new flow rate for the flow control device to adjust to.

Specific compositions, methods, or systems are intended to be only illustrative of the embodiments disclosed by this specification. Variation on these systems, methods, or embodiments are readily apparent to a person of skill in the art based upon the teachings of this specification and are therefore intended to be included as part of the inventions disclosed herein.

The present application claims priority to and the benefit of U.S. Provisional Application No. 63/378,981, filed Oct. 10, 2022, titled "METHODS AND SYSTEMS FOR ENHANCING PROCESSING OF HYDROCARBONS IN A FLUID CATALYTIC CRACKING UNIT USING A RENEWABLE ADDITIVE," U.S. Provisional Application No. 63/495,761, filed Apr. 12, 2023, titled "METHODS AND SYSTEMS FOR ENHANCING PROCESSING OF HYDROCARBONS IN A FLUID CATALYTIC CRACKING UNIT USING PLASTIC," and U.S. Provisional Application No. 63/495,748, filed Apr. 12, 2023, titled "METHODS AND SYSTEMS FOR ENHANCING PROCESSING OF HYDROCARBONS IN A FLUID CATALYTIC CRACKING UNIT USING A RENEWABLE ADDITIVE," the disclosures of which are incorporated herein by reference in their entirety. This application is also a continuation-in-part of U.S. Non-Provisional application Ser. No. 18/045,314, filed Oct. 10, 2022, titled "METHODS AND SYSTEMS FOR ENHANCING PROCESSING OF HYDROCARBONS IN A FLUID CATALYTIC CRACKING UNIT USING A RENEWABLE ADDITIVE," which claims priority to and the benefit of U.S. Provisional Application No. 63/262,342, filed Oct. 10, 2021, titled "METHODS AND SYSTEMS FOR ENHANCING PROCESSING OF HYDROCARBONS IN A FLUID CATALYTIC CRACKING UNIT USING A RENEWABLE ADDITIVE," the disclosures of which are incorporated herein by reference in their entirety.

The above detailed description is given for explanatory or illustrative purposes. It will be apparent to those skilled in the art that numerous changes and modifications can be made without departing from the scope of the inventive aspects of the technology. Accordingly, the whole of the foregoing description is to be construed in an illustrative and not a limitative sense, the scope of the invention being defined solely by the appended claims.

The invention claimed is:

1. A method of processing a gas oil in a fluid catalytic cracking (FCC) unit, the method comprising:
   introducing the gas oil and steam into a riser of a FCC unit;
   mixing the gas oil and the steam with a FCC catalyst fluidized in the riser;
   injecting one or more renewable feedstock into the FCC unit through one or more alternative locations of the FCC unit at one or more time periods, the one or more alternative locations including: (a) a stripper of the FCC unit, (b) a regenerator of the FCC unit, or (c) a combination of the stripper and the regenerator;
   cracking the gas oil and the one or more renewable feedstock into one or more FCC hydrocarbon products in the FCC unit, thereby to cause one or more surfaces of the FCC catalyst to be at least partially covered by coke so as to define a coked FCC catalyst;
   separating the coked FCC catalyst from the one or more FCC hydrocarbon products in the FCC unit; and
   passing the FCC hydrocarbon products to an outlet.

2. The method of claim 1, wherein the one or more alternative locations comprises a bed of coked FCC catalyst positioned within the regenerator of the FCC unit.

3. The method of claim 1, further comprising injecting one or more of a pre-stripping steam, a stripping steam, or a fluffing steam into the FCC unit, and wherein a portion of the one or more renewable feedstock is injected into the FCC unit along with one or more of the pre-stripping steam, the stripping steam, or the fluffing steam.

4. The method of claim 1, wherein the one or more alternative locations comprises a location in the FCC unit where catalyst densities are greater than about 30 lbs/ft$^3$.

5. The method of claim 4, wherein the injecting of the one or more renewable feedstock at the location in the FCC unit when the catalyst densities are greater than about 30 lbs/ft$^3$ causes an increase in residence time and promotes higher degrees of cracking the gas oil and the one or more renewable feedstock into lighter hydrocarbon products, and wherein the lighter hydrocarbon products comprise one or more of naphtha or liquefied petroleum gas.

6. The method of claim 1, wherein the one or more renewable feedstock comprises one or more of plastic-derived pyrolysis oil, plastic-derived hydrocarbons, biomass-derived pyrolysis oil, municipal waste-derived pyrolysis oil, vegetable based feedstock, animal fat feedstock, algae oil, sugar-derived hydrocarbons, or carbohydrate-derived hydrocarbons.

7. The method of claim 1, wherein the injecting of the one or more renewable feedstock into the one or more alternative locations generates selective yields for production of specified hydrocarbon products.

8. The method of claim 1, wherein specified hydrocarbon products include one or more of propylene, light olefins, transportation fuel, or other petrochemical feedstock.

9. The method of claim 1, wherein the injecting of the one or more renewable feedstock into the stripper of the FCC unit, the regenerator of the FCC unit, or the combination of the stripper and the regenerator, thereby increases delta coke.

10. The method of claim 9, wherein the one or more alternative locations further includes: (a) the riser of the FCC unit, (b) a reaction zone of the FCC unit, or (c) a combination of the riser and the reaction zone, and wherein the injecting of the one or more renewable feedstock into the riser of the FCC unit, the reaction zone of the FCC unit, or the combination of the riser and the reaction zone, thereby decreases the delta coke.

11. The method of claim 1, further comprising:
   determining, based on a signal received by a controller from a sensor or analyzer positioned at one or more of within the FCC unit, at an outlet of the FCC unit, or in fluid communication with the outlet of the FCC unit, one or more of a conversion, yield, or selectivity; and
   in response to a determination that one or more of the conversion, yield, or selectivity are less than a preselected amount, adjusting an amount of the one or more renewable feedstock injected into the FCC unit at the one or more alternative locations.

12. The method of claim 1, wherein one of the one or more renewable feedstock includes a blend of pyrolysis oil and wax.

13. The method of claim 12, wherein the blend comprises about 60% to about 100% pyrolysis oil and about 40% or less wax.

14. The method of claim 1, wherein, as an amount of the one or more renewable feedstock increases, coke yields decrease.

15. The method of claim 1, wherein the one or more renewable feedstock includes plastic-derived pyrolysis oil, plastic-derived hydrocarbons, or a combination thereof.

16. The method of claim 1, wherein specified hydrocarbon products include propylene, plastic precursors, or a combination thereof.

17. A method of processing a gas oil in a fluid catalytic cracking (FCC) unit, the method comprising:
during a FCC operation:
injecting a first selected amount of one or more renewable feedstock into one or more alternative locations of the FCC unit, the one or more alternative locations comprising one or more of an FCC reactor catalyst bed, an FCC catalyst stripper, at a nozzle located downstream of a gas oil injection point, or at a nozzle located upstream of the gas oil injection point;
cracking the gas oil and the one or more renewable feedstock into one or more FCC hydrocarbon products in the FCC unit, thereby to cause one or more surfaces of the FCC catalyst to be at least partially covered by coke so as to define a coked FCC catalyst;
passing the FCC hydrocarbon products to an outlet for further use; and
injecting a second selected amount of the one or more renewable feedstock into a regenerator of the FCC unit, thereby to regenerate the coked FCC catalyst.

18. The method of claim 17, wherein the injecting of a second selected amount of the one or more renewable feedstock into the regenerator of the FCC unit, thereby to regenerate the coked FCC catalyst comprises:
passing the coked FCC catalyst to the regenerator of the FCC unit,
introducing oxygen and the second selected amount of the one or more renewable feedstock into the regenerator,
combusting the coke from the coked FCC catalyst and the second selected amount of renewable feedstock in the regenerator, thereby to oxidize via the oxygen and produce a regenerated FCC catalyst and a flue gas, and
returning the regenerated FCC catalyst from the regenerator to a riser of the FCC unit.

19. The method of claim 18, wherein the one or more alternative locations (a) includes one or more locations of the regenerator and (b) enables introduction of the second selected amount of the one or more renewable feedstock into the regenerator.

20. A system for processing a gas oil in a fluid catalytic cracking (FCC) unit, the system comprising:
a riser having a first inlet to receive a gas oil stream, a second inlet to receive steam, a third inlet to receive a FCC catalyst, and a fourth inlet to receive a first renewable feedstock, the riser configured to be operated under cracking reaction pressure and temperature conditions to facilitate mixing and catalytic cracking of the gas oil stream in presence of the steam and the FCC catalyst, thereby to generate a plurality of FCC products and coked FCC catalyst; and
a reactor having (i) a fifth inlet to receive a second renewable feedstock, (ii) a FCC reaction zone connected to and in fluid communication with the upper portion of the riser and operated to continue the cracking of the gas oil stream in presence of the steam and the FCC catalyst, thereby to form more of the plurality of FCC products and more of the coked FCC catalyst, (iii) a separation zone to separate the plurality of FCC products from the coked FCC catalyst, and (iv) a first outlet to transport the plurality of FCC products to a fractionation zone, thereby to separate the plurality of FCC products into one or more of propylene, isobutene, butylenes, gasoline, distillate, diesel fuel, heating oil, slurry oil, or wet gas.

21. The system of claim 20, further comprising a regenerator connected to and in fluid communication with a second outlet of the reactor and having a sixth inlet to receive air, a third outlet being connected to and in fluid communication with the third inlet of the riser to supply a regenerated FCC catalyst to the riser, and a fourth outlet positioned to discharge a flue gas containing one or more of nitrogen, nitrogen oxides, carbon dioxide, carbon monoxide, or water vapor, the regenerator when being operated to oxidize coke on the coked FCC catalyst, thereby to produce the regenerated FCC catalyst and the flue gas.

22. The system of claim 21, further comprising a stripping zone connected to and in fluid communication with the second outlet and the regenerator, the stripping zone having a seventh inlet to receive a third renewable feedstock, the stripping zone when being operated to remove adsorbed and entrained hydrocarbons from the coked FCC catalyst prior to supply of the coked FCC catalyst to the regenerator.

23. The system of claim 22, further comprising the stripping zone having an eight inlet to receive stripping steam, and wherein a fourth renewable feedstock is injected into the stripping zone with the stripping steam.

24. The system of claim 21, wherein a third renewable feedstock is injected into the riser with regenerated FCC catalyst via the third outlet.

25. The system of claim 20, wherein a third renewable feedstock is injected into the riser with the steam.

26. The system of claim 20, wherein the fourth inlet is positioned downstream of or upstream of the first inlet.

27. The system of claim 20, wherein a third renewable feedstock is injected into one or more of the first inlet, the second inlet, or third inlet.

28. The system of claim 20, wherein fifth inlet is in fluid communication with the FCC reaction zone or the separation zone.

29. A controller to control processing a gas oil in a fluid catalytic cracking (FCC) unit, the controller comprising:
a first set of one or more inputs (a) in signal communication with one or more sensors positioned within one or more of a regenerator, a riser of the FCC unit, or a reactor of the FCC unit and (b) configured to receive signals from the one or more sensors indicative of a characteristic;
a first set of one or more inputs/outputs in signal communication with a first one or more flow control devices positioned on one or more inlets associated with one of the regenerator, the riser of the FCC unit, or the reactor of the FCC unit, such that the controller is configured to:
in response to the characteristic from one of the one or more sensors being less than or greater than a preselected threshold range, adjust, via a signal indicating a new flow rate for a flow control device, thereby to adjust to: (a) flow of renewable feedstock into one or more of the regenerator, (b) the riser of the FCC unit, or (c) the reactor of the FCC unit via one or more of the first one or more flow control devices; and
a second input/output in signal communication with a second one or more flow control devices positioned on an outlet associated with the regenerator, such that the controller is configured to:

in response to the characteristic from one of the one or more sensors being less than or greater than a preselected threshold range, adjust, via a second signal indicating a new flow rate for the second one or more flow control devices, thereby to adjust to flow of regenerated catalyst into the riser of the FCC unit via the second one or more flow control devices.

30. The controller of claim 29, wherein the characteristic comprises one or more of temperature, pressure, composition, flow rate, or yield percentages.

* * * * *